US006651659B2

United States Patent
Izuchukwu

(10) Patent No.: US 6,651,659 B2
(45) Date of Patent: Nov. 25, 2003

(54) AMBULATORY STORAGE SYSTEM FOR PRESSURIZED GASES

(76) Inventor: John I. Izuchukwu, 18002 Pine Canyon Ct., Wildwood, MO (US) 63005

( * ) Notice: Subject to any disclaimer, the term of this patent is extended or adjusted under 35 U.S.C. 154(b) by 0 days.

(21) Appl. No.: 09/864,058

(22) Filed: May 23, 2001

(65) Prior Publication Data

US 2003/0005933 A1 Jan. 9, 2003

(51) Int. Cl.[7] .............................. A62B 7/00; A62B 9/00; F17C 1/00; B65B 3/00; B65D 85/00
(52) U.S. Cl. ........................... 128/205.15; 128/205.22; 220/581; 206/0.6
(58) Field of Search ................ 128/200.24, 204.18, 128/205.13, 205.15–205.22; 220/581–585, 495.01, 589; 222/3; 206/0.6

(56) References Cited

U.S. PATENT DOCUMENTS

| | | | |
|---|---|---|---|
| 1,288,857 A | | 12/1918 | Farr |
| 2,380,372 A | | 7/1945 | Alderfer |
| 3,270,905 A | * | 9/1966 | Kroekel ................ 220/581 |
| 3,338,238 A | | 8/1967 | Warncke |
| 3,432,060 A | | 3/1969 | Cowley |
| 3,491,752 A | | 1/1970 | Cowley |
| 3,820,538 A | | 6/1974 | Nakanishi |
| 4,060,074 A | * | 11/1977 | Russo ................. 128/200.18 |
| 4,090,509 A | | 5/1978 | Smith |
| 4,101,045 A | * | 7/1978 | Roberts et al. ........ 220/560.12 |
| 4,154,234 A | | 5/1979 | Baker |
| 4,253,454 A | * | 3/1981 | Warncke ............... 128/202.26 |
| 4,438,764 A | * | 3/1984 | Eppolito ............... 128/204.18 |
| 4,800,923 A | | 1/1989 | Bartos |
| 4,932,403 A | | 6/1990 | Scholley |
| 4,964,405 A | | 10/1990 | Arnoth |
| 5,036,845 A | | 8/1991 | Scholley |
| 5,127,399 A | * | 7/1992 | Scholley ............... 128/204.18 |
| 5,280,780 A | | 1/1994 | Abel |
| 5,435,305 A | * | 7/1995 | Rankin, Sr. ............ 128/204.18 |
| 5,517,984 A | * | 5/1996 | Sanders ................. 128/200.24 |
| 5,529,061 A | | 6/1996 | Sanders |
| 5,881,725 A | | 3/1999 | Hoffman et al. |
| 6,003,744 A | * | 12/1999 | Culjak .................. 128/205.22 |
| 6,116,464 A | | 9/2000 | Sanders |
| 6,189,534 B1 | | 2/2001 | Zowtiak et al. |
| 6,230,922 B1 | * | 5/2001 | Rasche et al. ............. 220/586 |
| 6,405,728 B1 | * | 6/2002 | Van Hall et al. ......... 128/202.13 |
| 6,412,801 B1 | * | 7/2002 | Izuchukwu et al. ....... 280/250.1 |

* cited by examiner

*Primary Examiner*—William C. Doerrler
(74) *Attorney, Agent, or Firm*—Polster, Lieder, Woodruff & Lucchesi, L.C.

(57) ABSTRACT

A pressurized gas supply system includes a pressurized container which expands and contracts. The container includes a one-piece liner molded from a polymer which is reinforced by a high tensile fiber such as KEVLAR®. A valve is molded into the liner, and a regulator is connected to the valve. A hose, having a conserver positioned therealong, extends between the regulator and a fitting allowing a user to inhale gas from the container. The container is carried in a carrying bag, which can be in the form of a carrying case, a purse, or a back-pack.

14 Claims, 11 Drawing Sheets

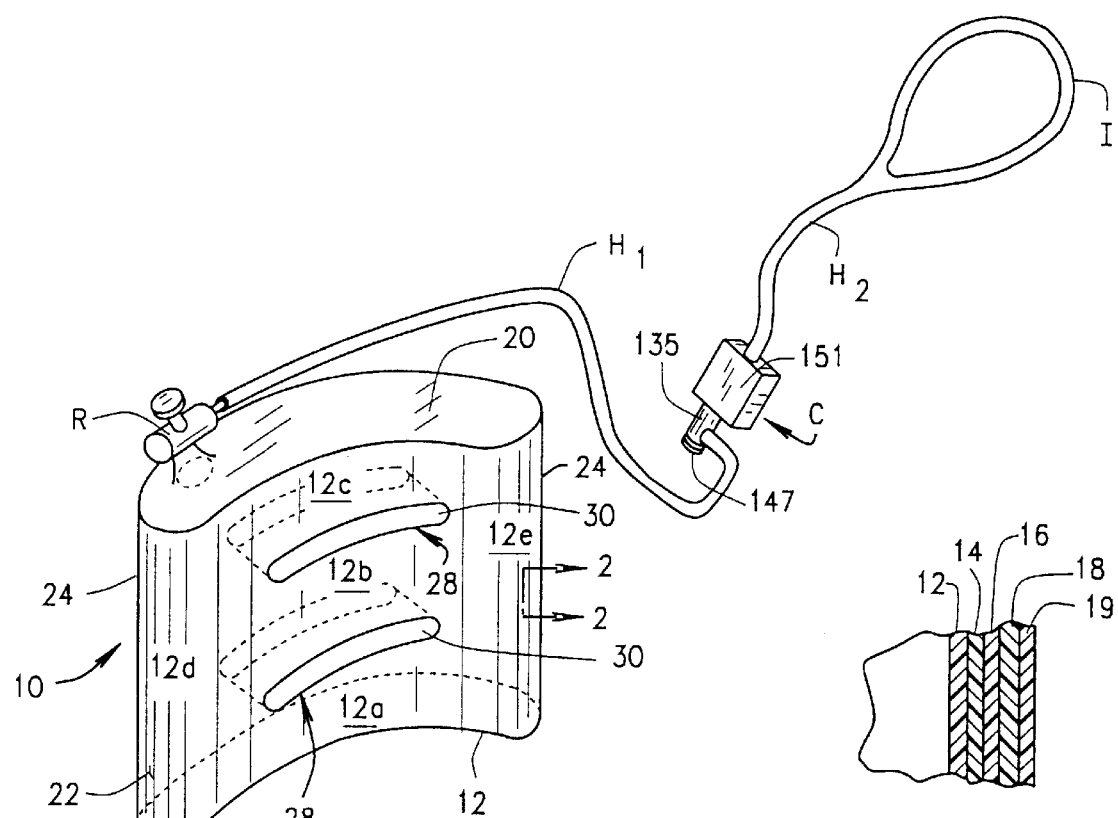
FIG. 1
FIG. 2
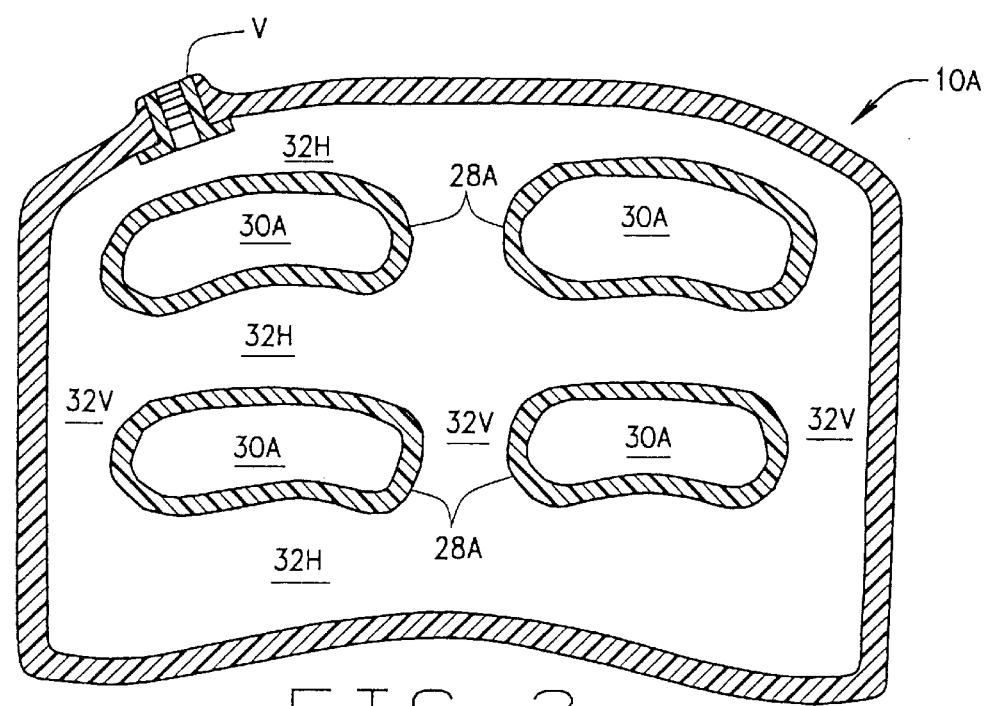
FIG. 3

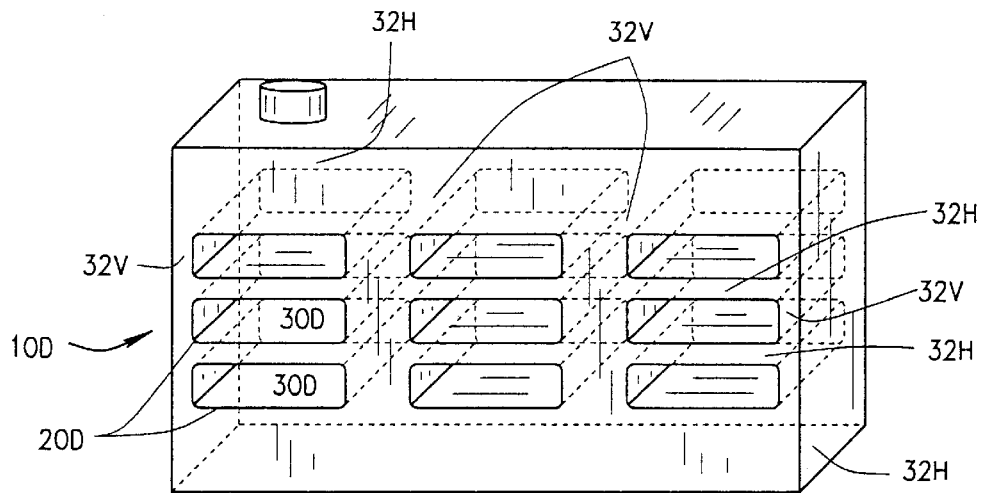
FIG. 5
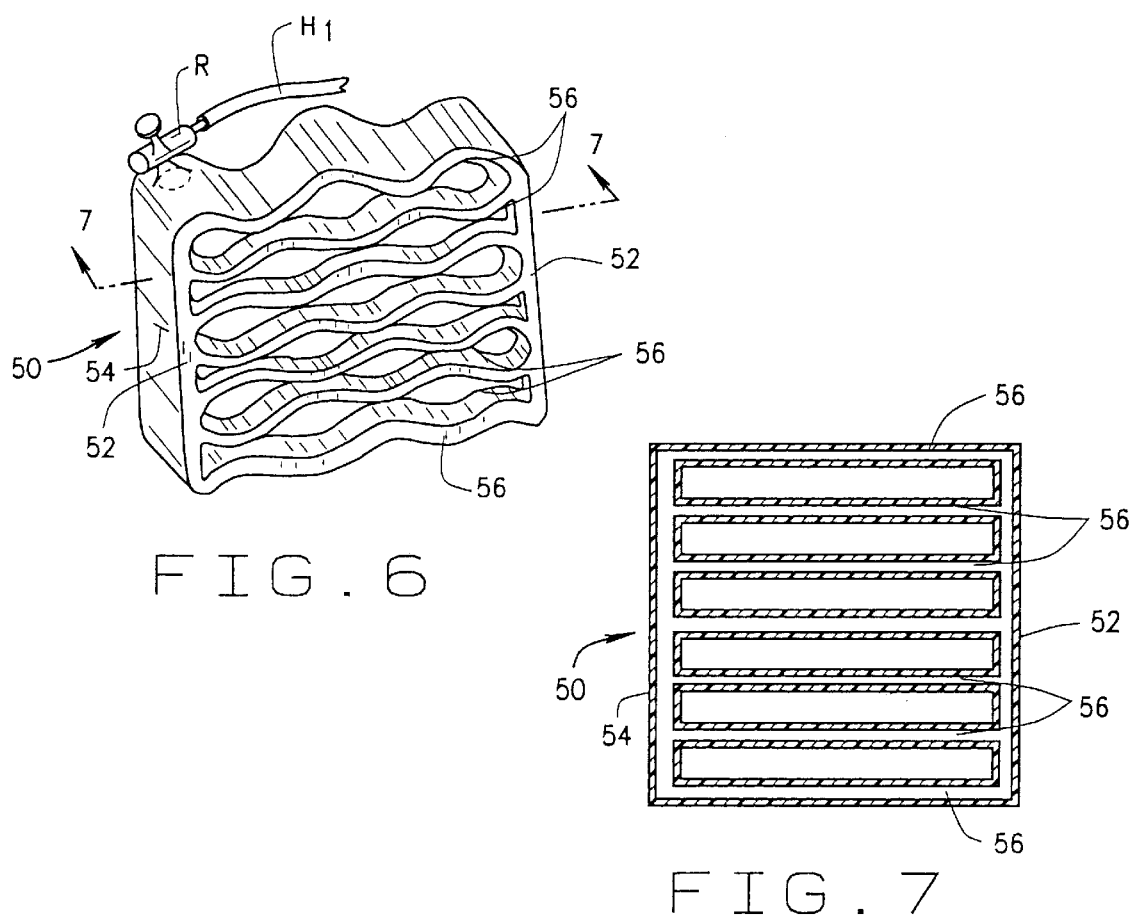
FIG. 6
FIG. 7

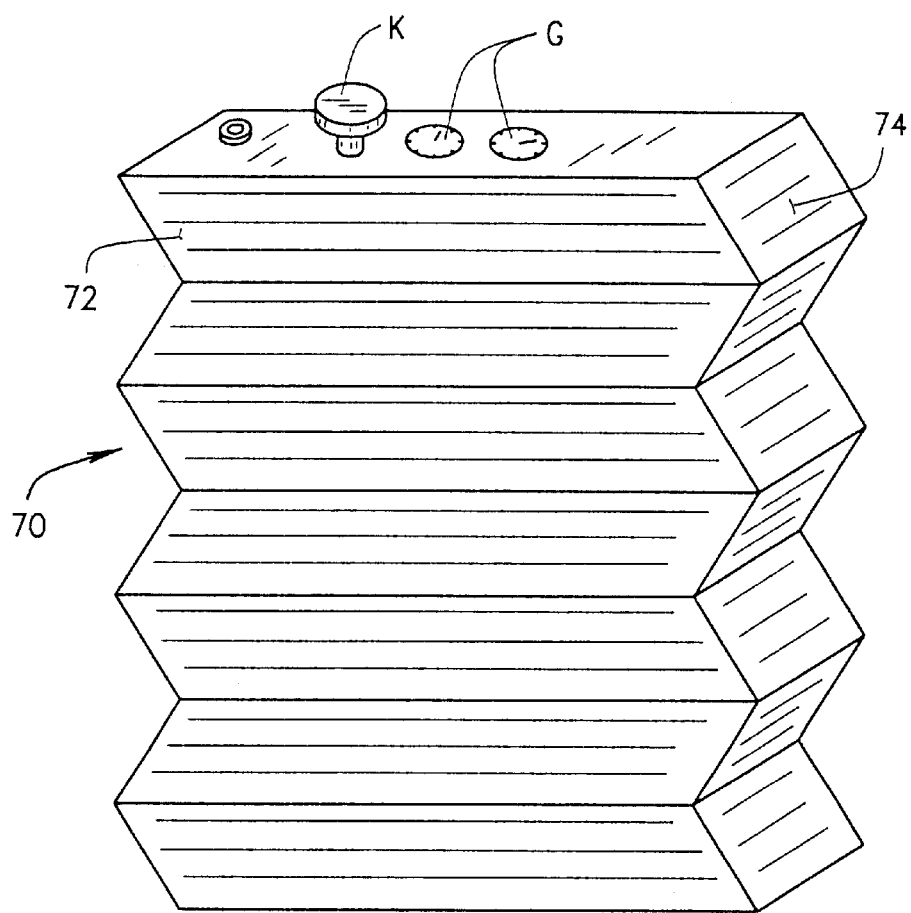
FIG. 10
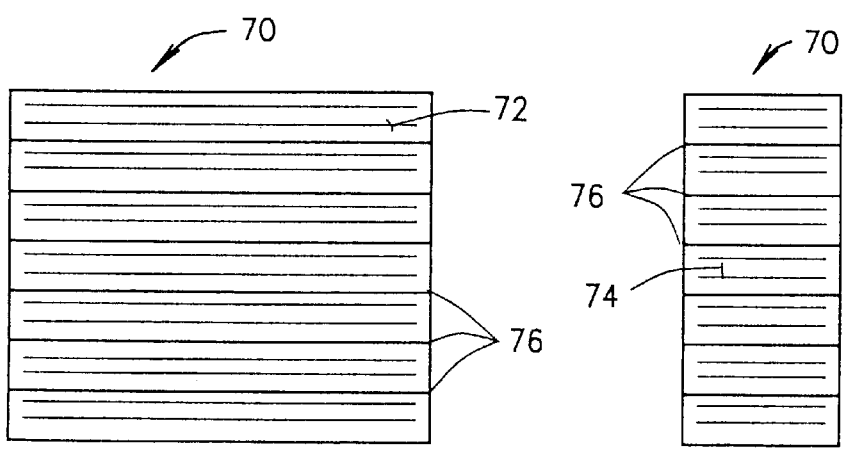
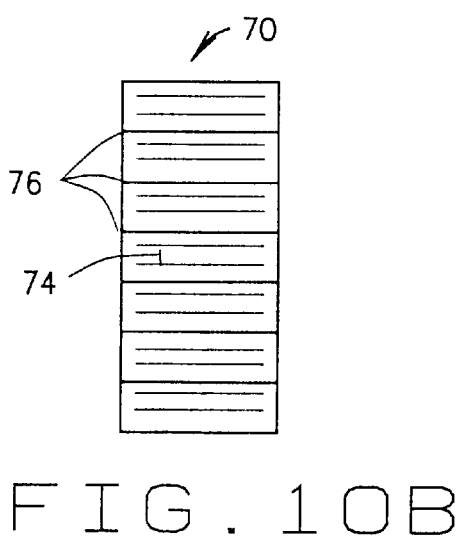
FIG. 10A  FIG. 10B

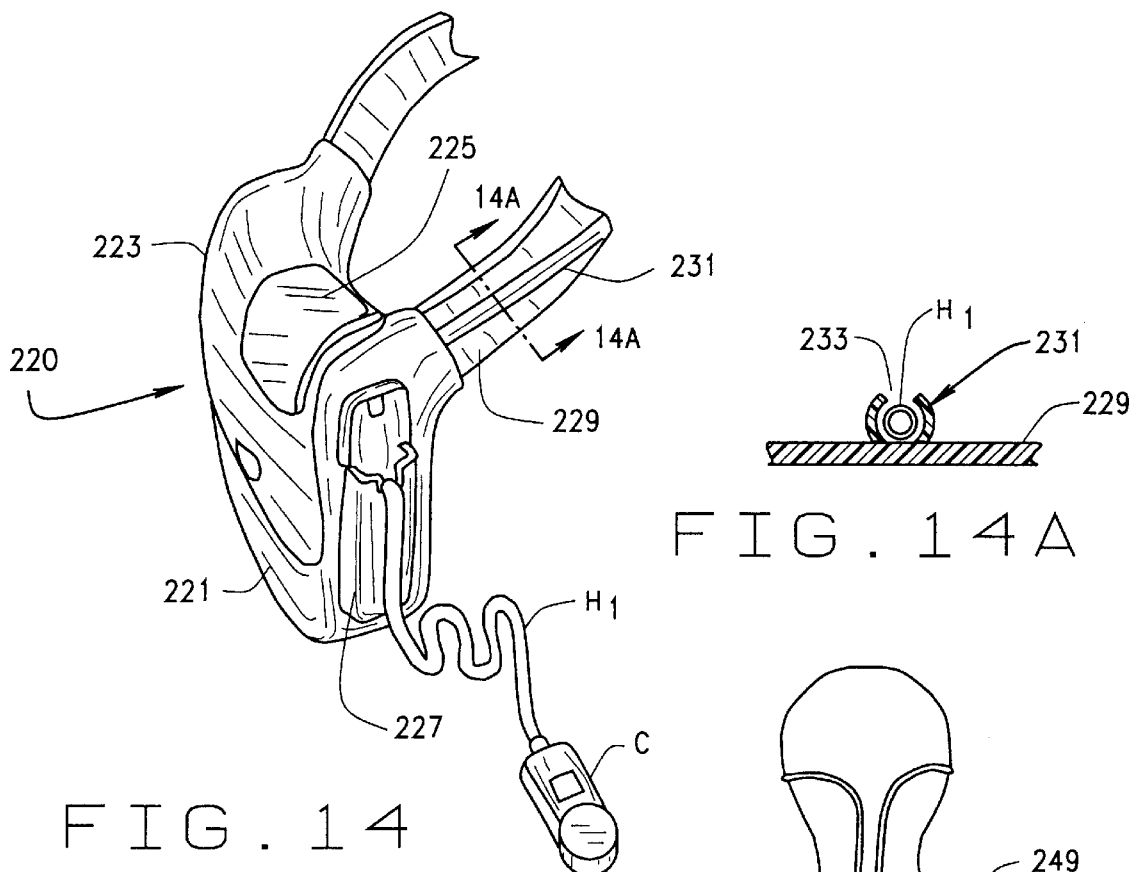
FIG. 14
FIG. 14A
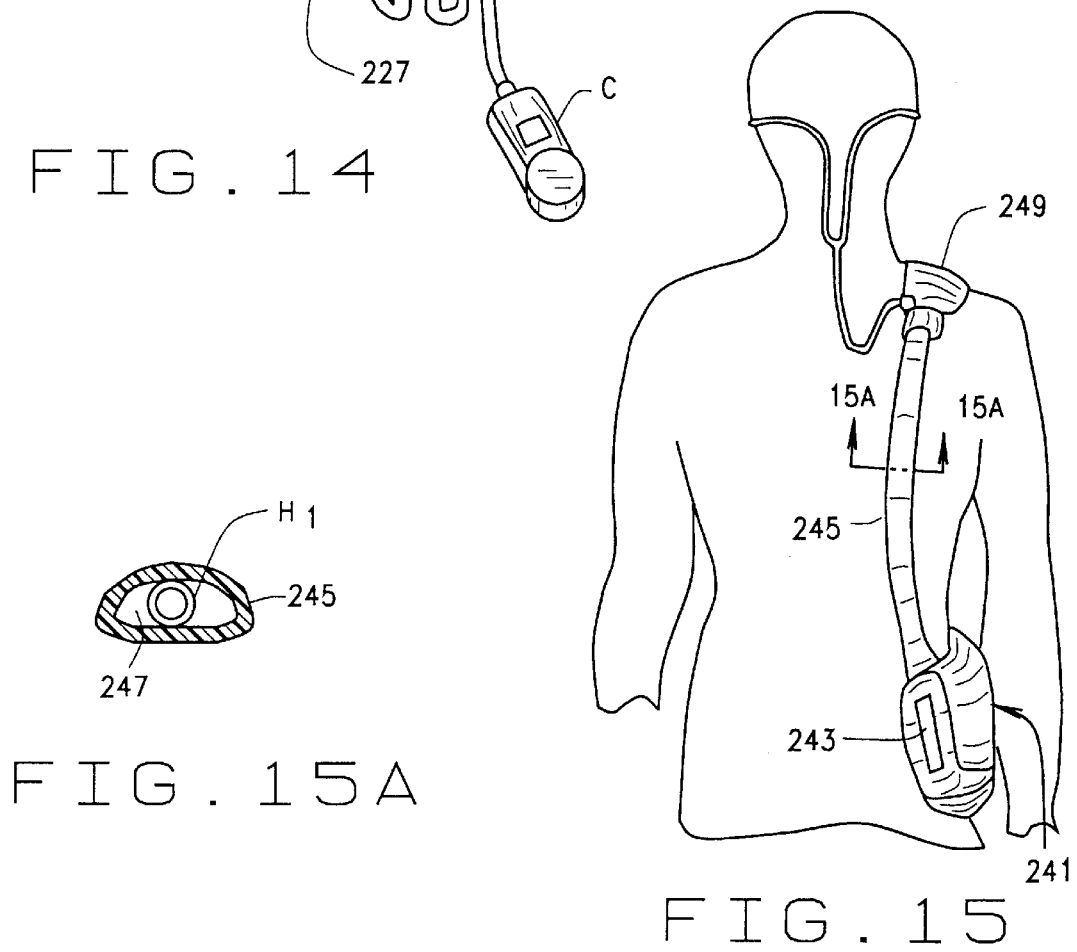
FIG. 15A
FIG. 15

AMBULATORY STORAGE SYSTEM FOR PRESSURIZED GASES

CROSS-REFERENCE TO RELATED APPLICATIONS

Not applicable

STATEMENT REGARDING FEDERALLY SPONSORED RESEARCH OR DEVELOPMENT

Not Applicable.

BACKGROUND OF THE INVENTION

This invention relates to storage systems for pressurized gasses, and, in particular, to an expandable, collapsible ambulatory storage system.

High-pressure gases are typically stored in steel or aluminum containers. For example, oxygen is stored in steel or aluminum containers (or cylinders) for use in aviation (spacecrafts, private, military and commercial airplanes), by scuba divers, in hospitals, emergency vehicles, and by patients requiring oxygen therapy. In aviation, oxygen is supplied in specially designed high-pressure canisters.

In the medical field supplemental oxygen is prescribed to patients who suffer from a variety of respiratory disorders, due to respiratory insufficiency or respiratory failures such as, obstructive pulmonary disease, chronic bronchitis, interstitial or restrictive lung disease, emphysema, congestive heart failure and during surgical operations. The typical modes of oxygen delivery are concentrators that concentrate atmospheric oxygen, pressurized canisters, high pressure cylinders made of steel or aluminum, or liquid oxygen systems that convert liquid oxygen to a gaseous state for ambulatory or domicile use. High-pressure cylinders are often wrapped with other high-tensile strength material for structural reinforcement such as carbon fiber, or other materials.

The steel or aluminum cylinders store gases at a range of pressure that depends on application. Supplemental oxygen storage devices for example store oxygen at a pressure of up to 3000 psi (pounds per square inch). For therapeutic use or other applications the pressure is lowered using a pressure regulator. In the case of therapeutic application it is regulated down to atmospheric pressure.

Existing gas storage devices suffer from many limitations, including economic, safety, ergonomic, human factors and environmental drawbacks. Aluminum or steel cylinders are expensive to manufacture and are not environmentally compatible. They are costly to distribute because of their weights and pose a safety hazard if ruptured or dropped. The economic attractiveness of these devices is diminished in a flat reimbursement healthcare system (such as under HMO's) and in situations where it is difficult to supply patients with the required cylinders, such as patients in remote locations.

Furthermore there is a high acquisition or capitalization cost associated with purchase of infrastructure needed for entry into this business because of the per-unit cost of steel or aluminum. This poses barriers to entry and ultimately limits competition with a resulting penalty in cost of care. These issues are compounded by the high cost of manufacture.

From a safety point of view, high-pressure storage devices made of steel or aluminum can fragment when ruptured. The fragments are effectively shrapnel, and can cause severe injury or even death to people in the vicinity of the cylinder when it ruptures.

Notwithstanding the long-term rehabilitative benefits of oxygen, patient compliance as well as adoption of high-pressure containers as a supplemental oxygen source has been a problem. The existing cylinders are not portable (they are too heavy), are uncomfortable to carry, or are esthetically displeasing. In response, several lightweight high-pressure gas storage containers made from a synthetic material have been proposed.

Scholley (U.S. Pat. No. 4,932,403) describes a container in the form of a continuous length of hose incorporating a series of expanded diameter storage sections and flexible connecting sections into its length. The storage chambers are interconnected by narrow bent conduits and attached to the back of a vest that can be worn by a person. The device embodies a pressure regulator at one end, which regulates supply of compressed gas to the mouth of the user.

Scholley's container includes an interior liner, constructed of flexible material, covered by braided fibers, which may be formed of a synthetic material such as nylon, polyethylene, polyurethane, tetrafluoroethylene, or polyester. The liner is covered with a reinforcing material, such Kevlar (an aramid fiber having a tensile strength three times the strength of steel) and impregnated by a protective coating of material such as polyurethane.

The Scholley container suffers from several limitations, making it impractical for high-pressure applications. The tubular shape of the independent containers does not provide adequate reinforcement for storage of high-pressure gas, and the narrow, bent conduits are unreliable when used in cyclical and repetitive filling and emptying applications. Furthermore it is costly and difficult to manufacture because of the required fittings, geometry of the conduits, amount of material and pieces that must be assembled. Another limitation of the Scholley container is that when the tubular high-pressure gas device is installed longitudinally within a vest, it is impractical. When the storage device is pressurized, it is as hard, rigid, and difficult to bend; and thus cannot be worn as clothing that overlaps the body.

Cowley (U.S. Pat. Nos. 3,491,752 and 3,432,060) describes a lightweight flexible pressure container made in the form of a coiled spiral tube. While compact, the device is limited to applications of short duration. Storage capacity cannot be increased by using a larger tube due to flexibility and weight penalties.

Farr (U.S. Pat. No. 1,288,857) describes a life preserver made from multiple interconnected cylinders, that are made from rubber, cloth or fabric. The geometry and configuration of the connecting pipes and cylinders pose severe challenges to manufacture and personal use, and as a result is infeasible.

Alderfer (U.S. Pat. No. 2,380,372) describes a portable container system that is built into a parachute pack to provide oxygen to parachutists. The container system includes a length of hose in the form of concentric coils that conform to the shape of the seat.

Warnke (U.S. Pat. No. 3,338,238) describes a multi-cell container which is flat or oval-shaped in cross-section. This container suffers from similar limitations as the other containers; i.e., the inability and/or expense to manufacture, and inability to conform to the body for personal use.

Sanders (U.S. Pat. No. 6,116,464) describes a container system, consisting of interconnected ellipsoidal chambers. A tubular core consisting of gas exchange apertures (for evacuation) connects the chambers. The Sanders container is also very expensive to manufacture.

Arnoth (U.S. Pat. No. 4,964,405) discloses a vest which can be worn by emergency personnel. The vest has a self-contained unit with a source of oxygen. Oxygen is stored in pressurized canisters in the front of the vest. The back of the vest includes collapsible channels through which the oxygen passes, and which contain $CO_2$ scrubbers to remove $CO_2$ from the gas being inhaled by the emergency personnel. These channels do not form or define pressurized containers for the oxygen.

No one, to my knowledge, has developed a light-weight pressurized container which is economical to manufacture, and is easily carried by the user.

BRIEF SUMMARY OF THE INVENTION

The feasibility of using a polymeric containers for medical, emergency or recreational gas transport has never been demonstrated or reduced to practice because of design, packaging and manufacturing challenges. I have developed a new container for the transport of gases, such as medical, emergency and recreational (scuba diving, mountain climbing, hiking, etc.) gases. Of course, other gases can also be transported or carried by the container. The container or vessel includes a liner constructed of polymeric material, which, in some embodiments possesses the appearance of a wine rack, with a hollow frame that is wound in an ellipsoidal fashion by a reinforcing fiber, but molded as one integrated whole.

The hollow container serves as the storage reservoir for compressed gas, and the conduit for filling and withdrawal of the contained gaseous fluid. The container is volumetrically sized for application specific capacity, embodying filling and withdrawal mechanisms, a means of regulating the delivery pressure of the gas to the user, as well as a conserving device that delivers gas on inspiratory demand as opposed to continuously. The regulator and filling means are located anteriorly on the container.

This container will hold compressed gases at pressures of more than 2000 psi. This is achieved by the arrangement of the chambers or passages, the walls of which provide structural strength to the container when pressurized, like trusses do for a bridge. Ordinarily, materials deform when subjected to forces beyond their elastic limit. The rib-like parallel arrangement of the passages acts as a structural reinforcement for the container, expanding during filling and collapsing as it is emptied. This arrangement also provides a spring-like effect that assures geometrical integrity when the acting force is removed. The liners are further reinforced with a fiber material.

The effect of the reinforcement of the line is to amplify the tensile and compressive strength of the interconnected reservoirs or passages, by boosting the elastic limit and spring constant of the material, thereby reducing the probability of premature rupture under tension and deformation due to compressive and tensile loads.

Briefly stated, the preferred gas container or tank of the present invention defines a volume for storing gas under pressure. The volume comprises at least one generally horizontal channel, and at least one generally vertical channel which are in fluid communication with each other such that gas in the container can flow freely between the channels. Preferably, there are at least two vertical channels (one on each side of the container) and at least two horizontal channels (a top and a bottom channel). There may also be diagonal channels.

In one embodiment, the container is rigid and has a top surface, a bottom surface, a front surface, a back surface, and side surfaces, the surfaces cooperating to define the volume. A plurality of slots extend between opposite walls of the container. The slots are hollow, and are defined by slot walls, and the slot walls, in turn, define the channels. The slots can be nearly any desired shape or combination of shaped. For example, the slots can be rectangular, round, kidney shaped, oval. The slot walls can be generally flat or outwardly curved.

In another embodiment of the container, the container expands upon pressurization and contracts as gas is emptied from the container. In this embodiment, the container includes interconnected conduits which define the horizontal and vertical channels. At least one of the horizontal and vertical conduits are expandable/contractible conduits which are movable between an expanded state when the container is pressurized and a contracted state when the container is unpressurized. The expandable/contractible conduits can be accordioned, or define at least a portion of a wave.

The container or tank includes a regulator, a conserver (which preferably is remote from the container). A first hose extends from the regulator to the conserver and a second hose extends from the conserver and has a fitting on the end thereof to enable a user to breath the gas from the container. Preferably, a carrier is provided for the container to facilitate carrying of the container by the user.

The carrier can be a back pack, a purse-type pack, or a waist-pack. No matter what type, the carrier is provided with a strap operable to secure the carrier to a person. The strap includes or defines a tube for holding the hose adjacent the strap for at least a portion of the length of the strap. In one embodiment, the strap is formed as a hollow tube and defines the tube. In another embodiment the tube extends along an outer surface of the strap and the hose is threaded through the tube. In an alternative embodiment, the tube includes a slot or groove through which the hose can be pressed.

The conserver includes a body having an inhalation chamber and an exhalation chamber which are in fluid communication with each other via a first port. A diaphragm in the inhalation chamber divides the inhalation chamber into a first part and a second part. A check-valve in the first port prevents the flow of oxygen from the inhalation chamber to the exhalation chamber.

An outlet passage to which the hose connects extends from the body. The outlet passage is in communication with both the inhalation chamber and the exhalation chamber via an outlet port and an exhalation port, respectively. A check valve is placed in the outlet port to prevent gas from entering the inhalation chamber from the outlet passage. A pressure activated exhalation valve in the exhalation port to selectively opens and closes the exhalation port.

A neck extends up from the body. The neck defines a chamber and includes an inlet to which a hose is connected to place the neck chamber in communication with the container. A plunger is axially movable in the neck chamber between an upward position and lowered position. The plunger has a stem which engages the diaphragm to move the diaphragm down as the plunger moves down. A seal around the plunger defines an air-tight seal between the plunger and the neck and divides the neck into a neck upper chamber and a neck lower chamber. The plunger is biased to an upward position by a spring.

A control passage extends from the neck to the exhalation valve to place the valve in communication with the neck chamber. A supply passage places the neck chamber in communication with the inhalation chamber second section;

the supply and control passages are reciprocally placed in communication with the neck upper chamber (and the container) and the neck lower chamber as the plunger reciprocates between its upward and lowered positions.

BRIEF DESCRIPTION OF THE SEVERAL VIEWS OF THE DRAWINGS

FIG. 1 is a perspective view of a pressurized container of the present invention;

FIG. 2 is a fragmentary enlarged cross-sectional view taken along line 2—2 of FIG. 1;

FIG. 3 is a cross-sectional view of an alternative embodiment of the container;

FIG. 5 is a perspective view of another embodiment of the pressurized container;

FIG. 6 is a perspective view of an expandable/collapsible pressurized container;

FIG. 7 is a cross-sectional view taken along line 7—7 of FIG. 6, but with the container pressurized;

FIG. 10 is a third embodiment of the expandable/collapsible pressurized container;

FIGS. 10A and 10B are side and front views, respectively, of the container of FIG. 10;

FIG. 14 is a side perspective view of a carrier adapted to hold a container of the present invention;

FIG. 14A is a cross-sectional view through a strap of the carrier of FIG. 14 and taken along line 14A—14A of FIG. 14;

FIG. 15 is a rear elevational view of a person wearing a carrier containing the pressurized container;

FIG. 15A is a cross-sectional view taken through the strap of the carrier of FIG. 15 and taken along line 15A—15A of FIG. 15;

Corresponding reference numerals will be used throughout the several figures of the drawings.

DETAILED DESCRIPTION OF THE INVENTION

Figure 4:
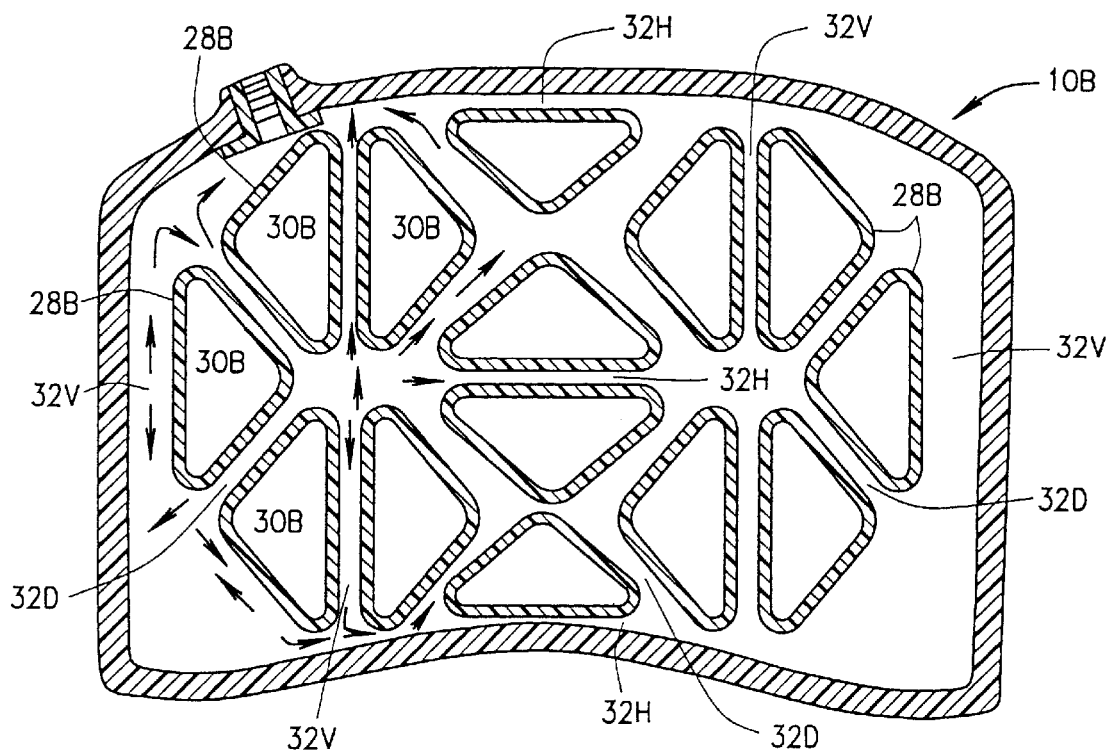
FIG. 4 is a cross-sectional view of another embodiment of the container.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. Although my system is described primarily in conjunction for use with therapeutic gases (i.e., oxygen), it will be appreciated that the container can be used with any other gas or gas mixtures which is pressurized. Thus, for example, the container also can be used to store hydrogen, helium, nitrogen, acetylene, etc. This list, of course, is exemplary only, it is not intended to be limiting, and it will be understood that other gases or gas mixtures can also be stored in the container of the present invention.

The feasibility of using a polymeric container for medical, emergency or recreational gases has never been demonstrated or made commercially available because of design, packaging and manufacturing challenges. I have developed a new polymeric container for use in a storage system for storing gases under high pressure. Several considerations were important in the design of the container. These considerations include:

1. Length of use: The duration of ambulation at a predefined rate of gas use by the user should be equal to or greater than traditional containers (i.e., cylindrical steel or aluminum containers).
2. Shelf life: The shelf-life of stored gas in the container should be at least 1 year (length of time before stored gas is totally diffused).
3. The container should be impervious to external contamination by infusion of gas through the walls of the container.
4. The container should be able to be pressurized and emptied many times with consistent reliability to a nominal pressure of 2000 psi.
5. The container should function reliability in varying temperature conditions.
6. The purity of stored gas should be maintained indefinitely (i.e., there should be no chemical reaction with the container; no leaching, no odor).
7. The container should weigh considerably less than existing high-pressure metal gas cylinders in the market.
8. The container should not fragment if ruptured.
9. The container should be environmentally friendly, recyclable and disposable.
10. The container should be easy to assemble (integrated unit with insert molded valve system)
11. The container should be inexpensive to manufacture.
12. The container preferably is ergonomically and aesthetically appealing.

A first illustrative embodiment of a pressurized container or bladder 10 of the present invention is shown in FIG. 1. The container 10 includes a molded inner liner 12. The liner 12 is formed from a polymer, such as linear low-density polyethylene (LLDPE), a low-density polyethylene (LDPE), or nylon. The liner 12 can also be made from Pebax®, a polyolefin-based polymer available from Atofina Chemicals of Philadelphia, Pa. Pebax®has carbon filler for added strength, and is more flexible than LLDPE; although LLDPE can be formed or bent more easily than Pebax®. The liner 12 can be made by injection molding, blow molding, rotomolding, or any other conventional method. Preferably, the container has a wall thickness of 0.05 to 0.07 inches (1.3 to 1.8 mm) to give the liner a desired volume to weight ratio.

The wall thickness can be reduced without sacrificing the strength of the liner, as a result of the proportional gain in tensile strength achieved with the fiber reinforcing jacket, as discussed below.

The polymeric liner 12 preferably contains additives such as stabilizers, antioxidants, UV stabilizers, colorants, plasticizers, fillers or reinforcements, flame retardants, other polymers, or any number of organic and inorganic additives used alone or in combination.

Plastic materials offer good thermal insulation due to their low thermal conductivity. In applications where heat dissipation is a problem, such as extreme temperature conditions that arise from thermal cycling during summer and winter conditions, attention must be paid to the insulative properties of the polymer, since temperature cycling also affects the pressure within the container and hence the container shelf-life. In this invention additives or reinforced thermoplastic material grades (composite materials) are used to significantly insulate the container from heat loss or heat gain.

Most plastic materials are flammable and will burn to some degree or decompose when subjected to combustive conditions. The design of an ambulatory storage system for pressurized gases must take these phenomena into consideration. A polymer such as polyethylene will ignite and burn readily, while a thermosetting phenolic will simply char. The flammability resistance of the present invention which consists of a polymeric container, constructed for example from polyethylene is improved using flame retardant additives.

Similarly, many plastic materials have poor weather resistance. The combined effect of ultraviolet energy (from sunlight) and oxidation can lead to deterioration in color and other properties over time. This is of concern in the design of a long term ambulatory storage system for pressurized gases that is intended for long term internal and outdoor use. In this invention, the long term weather resistance is improved significantly using ultraviolet stabilizers and antioxidants as additives.

The liner 12 can also be formed from a matrix composite, such as a carbon fiber or a resin/fiber combination. The carbon fiber or resin/fiber combination is embedded within a matrix of a thermosetting or thermoplastic polymer.

Three other polymeric materials have been evaluated that produce good results, when biased with a high tensile strength fiber material such as Kevlar, namely: PVC (polyvinyl chloride), Pellethane, a thermoplastic polyurethane elastomer available from Dow, and Texin, a thermoplastic polyurethane resin from Bayer Plastics Division. All three materials present a high barrier to gas diffusion and effusion; that is, gas can be stored within a container made of either material for a long period of time with negligible loss of content due to permeation. Permeability is defined as the volumetric flow rate of gas through a membrane barrier such as the wall (or liner) of the container. In the case of this invention the wall material is a polymeric membrane or carbon fiber matrix and the permeant gas is therapeutic oxygen (or other gas stored within the container). The preferred permeability value for polymeric membranes is 0.2 Barriers or less. Two of the candidate materials, namely Pellethane and PVC conform most to the design requirements of a fiber reinforced high pressure gas storage container system, and as a result are the preferred materials.

A protective, moisture impervious film 14 is applied to the polymeric or matrix composite liner 12 to substantially prevent the pressurized gas (which can be at pressures of up to 2000 psi or more) from external contamination by moisture due to atmospheric humidity, accidental or intentional abuse that spills liquid over the container 10, or contamination by external gasses. The film 14 can be epoxy, santoprene, or polyurethane.

Because polymeric materials have a lower tensile strength than steel or aluminum, without an external biasing material to elevate the theoretical yield point of the container, when subjected to internal loading, most polymers will yield and rupture, under tensile stress before reaching operating pressure of 2000 psi. Worse yet, to achieve a safety factor of two (2) or more would be near impossible without an external reinforcing or biasing material. To achieve tensile strength as good as the traditional baseline materials (i.e., aluminum and steel), while reducing the overall weight of the container 10, a reinforcing jacket 16 is applied to the liner 12. The film 14, which is an adhesive, secures the jacket 16 to the liner 12. The adhesive coating 14 is applied to the liner 12 under pressure to glue the jacket 16 to the outside of the liner.

The jacket 16 is made from a high tensile strength fiber material, such as KEVLAR® (available from DuPont under the product codes KEVLAR 29 and KEVLAR 49), S-Glass, E-Glass, Steel Wire, HS Polyethylene, and High-Tenacity Carbon (which has an initial modulus of 1350 gm/denier, a tenacity of 100 gm/denier, a flex life of 100%, and an elongation at break of 1.2%–1.5%). These materials are preferred because of their specific tensile strength and high decomposition temperatures. The jacket 16 is formed preferably from threads of the material which are wrapped about the container so that the direction of the thread will be perpendicular to the radial force exerted by the gas in the container. For the containers of FIGS. 1–5 (which as discussed below, are rigid) the jacket 16 can be molded about the liner 12.

KEVLAR® fibers are made of long molecular chains produced from poly-paraphenylene terephthalamide. The chains are highly oriented with strong interchain bonding which result in a unique combination of properties which give the fibers high tensile strength coupled with light weight. KEVLAR® is five times stronger than steel on an equal weight basis, yet at the same time flexible and comfortable.

Another attribute of KEVLAR® is that it is hydrolytic and degradation can occur when exposed to strong acid bases. At neutral pH (pH 7), the filament tenacity remains virtually unchanged after exposure at 149° F. (65° C.) for more than 200 days. The further the pH deviates from a pH of 7, the greater the loss in tenacity. Strength loss determination is accomplished by comparing strength data at room temperature for control and exposed yarn.

There is a tendency for most fibers to regain moisture depending on the relative humidity (RH) and temperature. Most fibers like KEVLAR® have a tendency to pick up or give off ambient moisture content at a given temperature and humidity level. Relative humidity also has a significant effect on the rate of moisture absorption by KEVLAR® and the equilibrium level reached. The higher the relative humidity, the faster KEVLAR® absorbs moisture during the initial phase of moisture gain and the higher the final equilibrium level. Bone-dried KEVLAR® is preferably used because it will reach a slightly lower equilibrium moisture level than fiber that has never been bone dried.

The container preferably is sealed from moisture and environmental chemical exposure by a coating 18. While KEVLAR is chemically stable under a wide variety of exposure conditions, certain strong aqueous acids, bases and sodium hypochloride can cause degradation, particularly over long periods of time and at elevated temperatures. KEVLAR does not melt but decomposes at relatively high temperatures (800° F. to 900° F. [427° C. to 482° C.]) in air and approximately 1,000° F. (538° C.) in nitrogen, when tested with a temperature rise of 10° C. per minute. For this reason it is important that the KEVLAR material be shielded by a non-thermal absorbing material to maintain its' specific weight to strength property. Thus, an outer coating 18 is applied over the jacket 16. The coating 18 is made from a material that is non-gas absorbing, and will not readily conduct heat (so that the coating 18 will not act as a heat sink). In the case of fiber composite matrix container, a polymeric liner material shields the stored gas from contact with the internal walls of the container and reaction with the carbon fiber as well as prevents contact with external gases and moisture contamination.

The material used for the coating 18 should not have a melt temperature higher than the reinforcing fiber material of the jacket 16. The high temperature to which the reinforcing fiber material is exposed during application of the coating 18 may alter the engineering properties and strength of the jacket 16. The coating 18 can be made from a fluorocarbon, such as Teflon which will add stiffness to the assembly and have a higher melting temperature than other elastomeric materials. The coating 18 can also be made from polyurethane. Polyurethane can be sprayed over the jacket 16 to keep the strands or threads which make up the jacket together, as well as to provide protection from moisture and ultraviolet rays. Polyurethane can be applied at a relatively low temperature, and a catalyst can be incorporated to speed up the curing process after the polyurethane has been applied to the container jacket 16. Polyurethane is a trough UV-resistant material, which can be applied in a wide range of durometers. This makes polyurethane a good choice for use as the outer protective coating 18.

Additionally, an outer fire retardant fabric or coating 19 is applied around the coating 18 to protect the container from rapid ignition in the event of accidental contact with flames due, for example to smoking. The fire retardant material is also preferably water repellant. The coating 18 shields the jacket 16 from ultra violet radiation and extreme temperatures, which have been shown to reduce the tensile strength of fiber. Fire retardant chemicals can be incorporated into the coating 18, to give the coating 18 the same properties as the coating 19. In this instance, the coating 19 would not be required.

If the liner 12 is made from carbon fiber, then the jacket 16, and the adhesive layer 14 are not needed, and can be omitted. In this case, the coating 18 is applied directly to the liner 12.

To complete the container 10, the container is provided with a valve V. Because the liner 12 is molded, the valve V can be, and preferably is, molded into the liner 12 as the liner is formed. The valve V is a standard valve for use with high pressure cylinders and includes a threaded throat. A regulator R is connected to the valve to reduce the pressure of the gas exiting the container close to atmospheric pressure so that a user can breath in the gas. Preferably, the regulator is recessed in the container, as seen in FIG. 1 to provide a low profile. Regulators are common in the industry, and are available for example, from Essex Industries, Inc. of St. Louis, Mo. The regulator can be threaded to the valve. Alternatively, the regulator and valve can be formed as a unitary, one-piece assembly.

A conserver C is provided to provide for on-demand supply of the gas, so that gas is released from the container only when the user is inhaling, and not when the user is exhaling. Thus, a continuous output of gas is prevented, and hence, the gas supply will last longer. The conserver C can be connected directly to the output of the regulator. However, as shown in FIG. 1, the conserver C preferably is remote from the regulator, there being a hose H1 extending from the regulator to the conserver C, and a second hose H2 extends from the conserver C to an inhalation device I, such as a cannula. The remote conserver C allows for the cannula to be clipped to, for example, a user's belt. As is known, the cannula C has prongs which extend into an individual's nose to allow the individual to breath oxygen from the container 10. The cannula C could be replaced with a closed system such as a facial mask, nasal cup, or mouth-piece which covers the mouth and/or nose, such as used by scuba-divers, emergency personnel, for administration of medical gases to patients (such as patients who suffer from apnea, or have other breathing problems) who require positive air pressure to assist breathing, or in other situations in which a closed system is required.

The conserver can be a commercially available conserver, such as is available from Victor Medical of Denton, Tex. under the name $O_2$nDemand, or from Mallinckrodt Medical under the name OxiClip. However, preferably, the conserver is one such as shown in FIG. 11.

Figure 11:
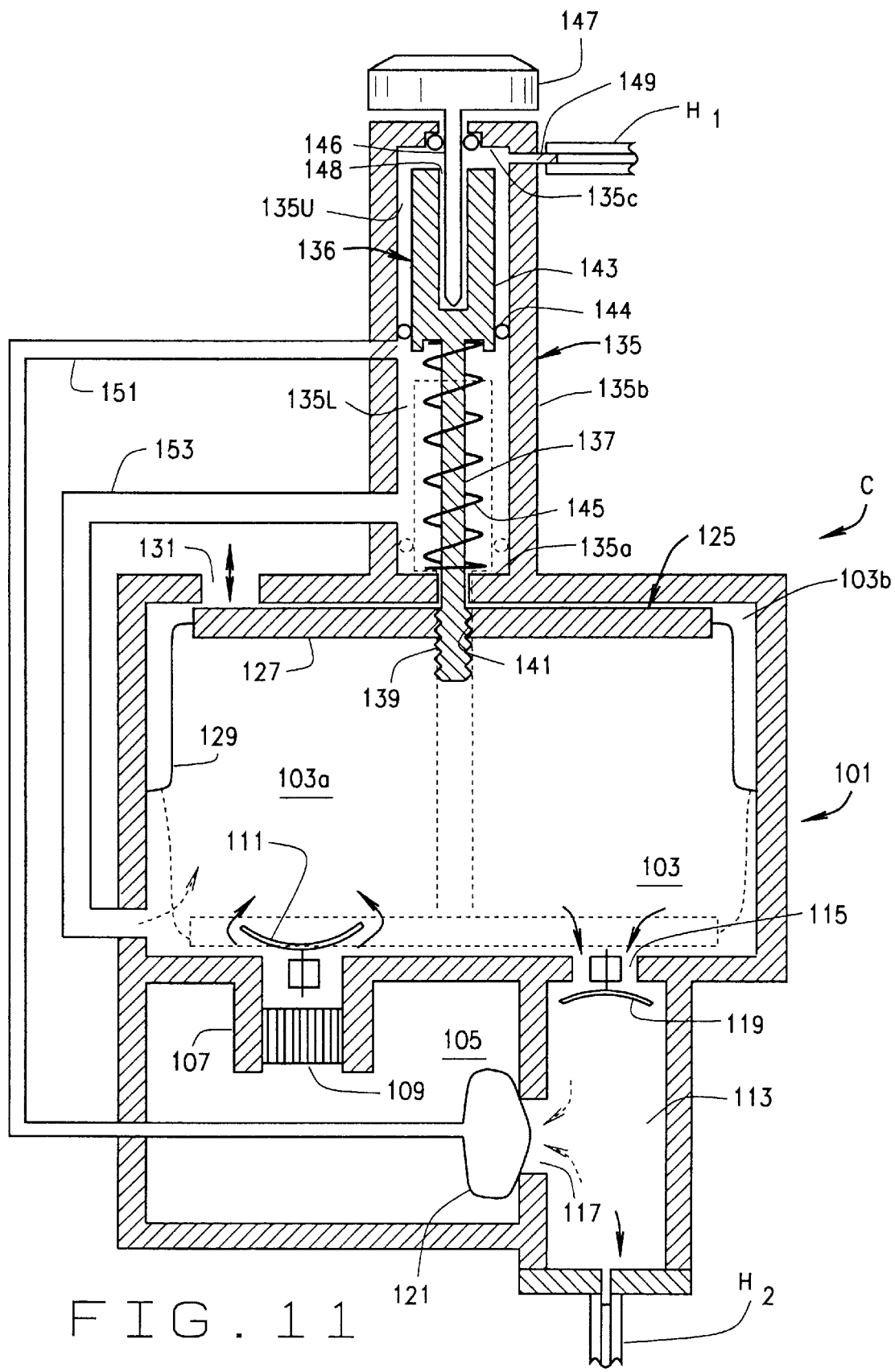
FIG. 11 is a diagram of a pneumatic conserver for use with the gas storage system.

The conserver C of FIG. 11 has a body 101 defining two chambers: an inhalation chamber 103 and an exhalation chamber 105. The chambers 103 and 105 are in communication with each other via a port 107 having a filter 109. The port 107 is opened and closed by a check-valve 111. A passageway 113 is in communication with the inhalation chamber 103 via an inhalation port 115 and with the exhalation chamber via an exhalation port 117. A check valve 119 is positioned at the inhalation port 115 to open and close the port 115; and an exhalation valve 121 is positioned at the exhalation port 117 to open and close the exhalation port. The passageway 113 terminates in a connector, so that the hose H2 can be connected to the passageway 113, to place the inhalation device (cannula) in communication with the conserver C.

A diaphragm 125 is mounted in the inhalation chamber 103. The diaphragm 125 includes a diaphragm plate 127 and a flexible membrane 129 which extends between the periphery of the plate 127 and the side walls of the chamber 103. The diaphragm 125 divides the chamber 103 into two sections: a lower or inhalation section 103a which is in communication with the passageway 113, and an upper section 103b, which is placed in communication with the atmosphere via a port 131.

A neck 135 extends up from body 101. The neck 135 includes a floor 135a, side walls 135b, and a top 135c, and houses a piston 136 having a piston stem 137 and a piston head 143 extending up from the top of the stem. The piston stem 137 has a threaded lower end 139 which is received in a threaded opening 141 in the diaphragm disk 127. An O-ring 144 near the bottom of the piston head 143 forms an air tight seal between the piston stem head 143 and the neck walls 135b. The O-ring 144 effectively divides the neck in to an upper neck chamber 135U and a lower neck chamber 135L.

A spring 145 extends between the bottom of the piston head 143 and the neck floor 135a, and biases the piston 136 and diaphragm 125 to a normally upward position, as shown in FIG. 11. A volume control knob 147 is external of the conserver neck, and is operatively connected to the piston head 143, such that rotation of the knob 147 will rotate the stem head 143 and stem 137. As can be appreciated, rotation of the stem will change the relative position of the diaphragm disk 127 in the chamber 103, and hence will adjust the size and volume of the chamber 103a.

The knob 147 includes a shaft 146 which is received in an opening 148 in the top surface of the piston head 143. The shaft 146 is fixed to the head 143 in the opening 148 so that rotation of the knob 147 will rotate the piston 136 to alter the position of the diaphragm 125, while allowing for the piston to move axially relative to the knob shaft 146. For example, the shaft 146 can include an axial rib which is received in an axial groove in the piston opening 148. The shaft 146 passes through an opening in the top wall 135c of the stem. An O-ring is seated around the knob shaft 146 to form an air tight seal between the shaft and the stem top wall to substantially prevent gas from escaping through the shaft opening in the stem top wall.

A connector 149 is near the top of the valve neck 135 and is connected to the hose H1. Hence, gas from the container 10 enters into the conserver C through the neck upper chamber 135U. An exhalation valve control passage 151 places the exhalation valve 121 in fluid communication with the neck 135. The valve 121 is a diaphragm or balloon valve, and when gas enters the passageway 151, the valve 121 closes the exhalation port 117. The connection between the passageway 151 and the neck 135 is near the O-ring 144, so that as the piston 136 reciprocates axially within the neck, as described below, the passageway 151 is alternately in communication with the neck upper chamber 135U and the neck lower chamber 135L. An inhalation supply passage 153 places the neck in communication with the inhalation chamber 103a. Again, the supply passage 153 is placed alternately in communication with the neck lower chamber 135L and the neck upper chamber as the piston reciprocates within the neck 135.

As noted above, the conserver C is normally biased by the spring 145 to the position shown in FIG. 11, wherein the exhalation valve control passage 151 is in communication with the neck lower chamber 135L. When gas (generally an oxygen-nitrogen mixture) enters the neck upper chamber 135U via the connector 149, the gas will fill, and pressurize, the neck upper chamber 135U. When the pressure in the neck upper chamber 135U exceeds the force of the spring 145, the piston 136 will be forced axially downwardly within the neck 135. When the piston moves axially downwardly, with reference to FIG. 11, the O-ring 144 passes the junction to the exhalation valve control passage 151 to place the control passage 151 in communication with the neck upper chamber 135U, and hence with the supply of gas. Thus, gas will flow through the control passage 151 to pressurize the valve 121 to close the exhalation port 117 to the passageway 113. Additionally, as the piston moves axially downwardly, the diaphragm 125 will also be urged downwardly. The downward movement of the diaphragm 125 will reduce the size of the chamber 103a, causing the valve 111 to the exhalation chamber to close, and the valve 119 to the passageway 113 to open. Thus, gas will pass through the passageway 113 to the hose H2, and the patient (or user) will be supplied with oxygen. When the piston 136 is at the end of its travel, as shown in phantom in FIG. 11, the O-ring 144 is below the entrance to the supply passageway 153, to place the inhalation passageway in communication with the neck upper chamber 135U, and hence the supply of gas. The inhalation passageway 153 is greater in diameter than the control passage way 151. Hence, when the piston 136 is at the end of its travel, the volume of gas in the neck upper chamber 135U is quickly dumped into the inhalation chamber 103a through the passageway 153. The filling of the inhalation chamber 103a and the spring 145 act in concert on the diaphragm 125 and the piston 136 to return the piston 136 and diaphragm 125 to the normal position. As the piston and diaphragm travel to the normal position, the O-ring 144 passes the exhalation valve control passage 151, to place the passage 151 in communication with the neck lower chamber 135L. The exhalation valve 121 will then become depressurized, and, as the patient (or user) exhales, the valve 119 to the inhalation chamber 103a will close; gas in the passageway 113 will enter the exhalation chamber 105; the valve 111 between the exhalation chamber 105 and the inhalation chamber 103a will open; and the exhalation chamber will be placed in communication with the inhalation chamber. The gas in the exhalation chamber 105 will then pass through the filter 109 and into the inhalation chamber 103a. The filter 109 can be provided to remove moisture, $CO_2$, or other desired elements from the gas passing from the exhalation chamber to the inhalation chamber.

The piston 136 and diaphragm will continue to reciprocate between the raised (normal) and lowered positions to deliver gas through the hose H2 to the inhalation device I on a cyclical basis. The rate of the cycle depends on the pressure set at the regulator R, the force of the spring 47, and the volume of the chamber 103a (i.e., the setting of the flow control knob 147). As can be appreciated, as the pressure from the regulator is increased, the cycle time of the conserver C will shorten.

While the preferred conserver C is pneumatic, as illustrated in FIG. 11, controlled delivery of oxygen to the patient can also be achieved with a smart electronic device. That is, the conserver can be electronic, as opposed to pneumatic.

Figure 11A:
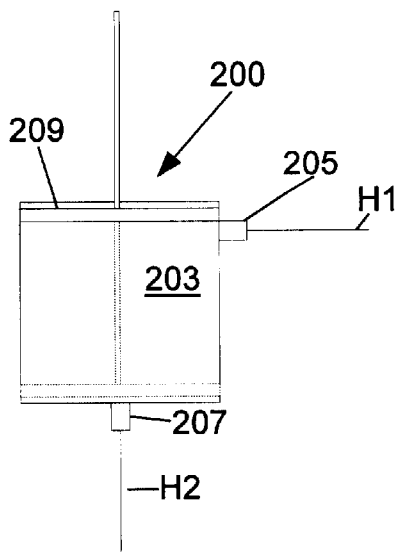
FIG. 11A is a diagram of an electronic conserver.

An electronic conserver 200 is shown in FIG. 11A. The conserver 200 includes a sensor body 201 defining a chamber 203. An inlet 205 placed the chamber in communication with the container or tank by the hose H1. The hose H2 is connected to an outlet 207. A piston 209 reciprocates in the chamber between a raised position and a lowered position (shown in phantom in FIG. 11A). In the raised position, the inlet 205 is in communication with the chamber 203 to fill the chamber with oxygen. The piston 209 is activated, for example, by a solenoid or other controller 211, which extends and retracts the piston 209 to reciprocate the piston within the chamber. As can be appreciated, when the piston 209 is extended, oxygen is forced out of the outlet 207 to deliver oxygen to the user. When the piston retracts, the chamber is placed in communication with the container to fill the chamber with oxygen. The activation of the solenoid, and hence the piston, is controlled by a CPU 213. The CPU emits a timed or periodic signal to activate the solenoid 211, and hence, pump oxygen out the outlet 207. As can be appreciated, the shorter the interval between signals, the faster oxygen will be pumped.

Figure 11B:
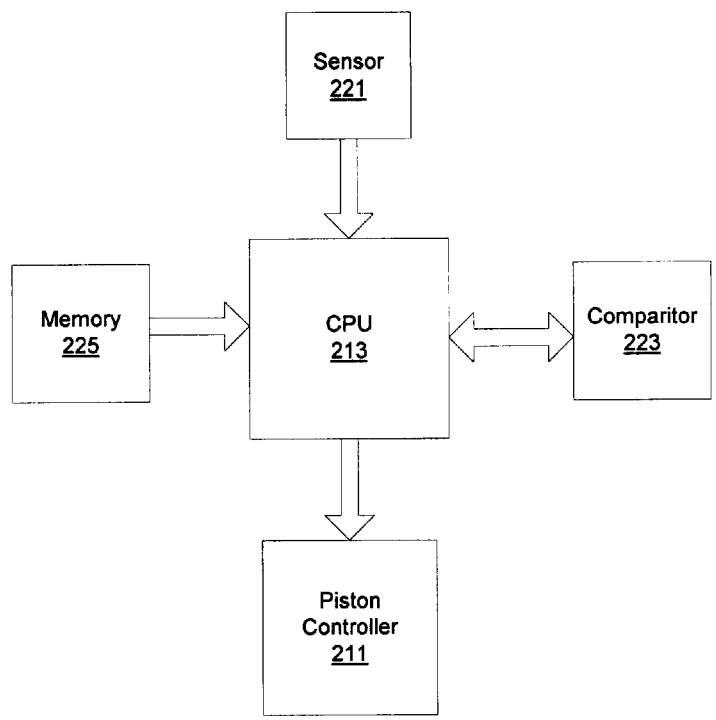
FIG. 11B is schematic of the electronic conserver.

A block diagram of the conserver 200 is shown in FIG. 11B. To determine the rate at which oxygen should be pumped, the conserver 200 includes a sensor 221, such as a linear sensor, in the nasal cannula or oxygen mask to measure either the oxygen or carbon-dioxide content of exhaled gases. The sensor 221 generates a signal representative of the composition of the exhaled gas in the cannula; and the CPU 213 receives the signal from the sensor. Preferably, the sensor 221 senses the $CO_2$ content of the exhaled gas. To obtain an accurate determination of the $CO_2$ content of the exhaled gas, the sensor is positioned on or near the nose tube of the nasal cannula. By positioning the sensor 221 in close proximity to the nose (or preferably in the nose) the sensor 221 will be able to obtain an accurate determination of the $CO_2$ composition of the exhaled gas in the open system presented by the nasal cannula.

A target or desired gas composition of the exhaled gas is stored in a memory or storage device 225. The storage or memory device 225 is programmable, so that the stoichiometric composition of the target exhaled gas can be altered, if necessary. A comparitor 225 compares the gas composition of the exhaled gas to the target gas composition and outputs a swing signal which is received by the CPU 213. The swing signal is used to adjust timing or rate of the signal sent to the solenoid 211 to increase or decrease the flow of oxygen to the user. The adjustment of the oxygen flow is based on the difference between the compositions of the exhaled gas ($G_e$) and the target fractional gas ($G_t$). Thus, based on the swing signal, the CPU will generate increase or decrease the interval between activation signals which are sent to the solenoid 211, to increase or decrease the flow of oxygen to the user. For example, during exercise, it has been shown that the demand for oxygen consumption goes up; thus we would expect that the oxygen content of the exhaled gases to be substantially lower than the composition that would be found in a sedentary activity level, or during sleep. Similarly, carbon-dioxide composition of the exhaled gases would go up when metabolic rate goes up (due to exercise). Thus, when the $G_e$ falls below $G_t$, the rate of gas delivery is increased, and when $G_e$ is greater than $G_t$, the rate of gas delivery is decreased. The target stoichiometry or composition exhaled gas ($G_t$) can be pre-programmed and altered if necessary. The value of $G_t$ depends on several factors, including patient disease, disease state, history and demographic information).

Figure 12:
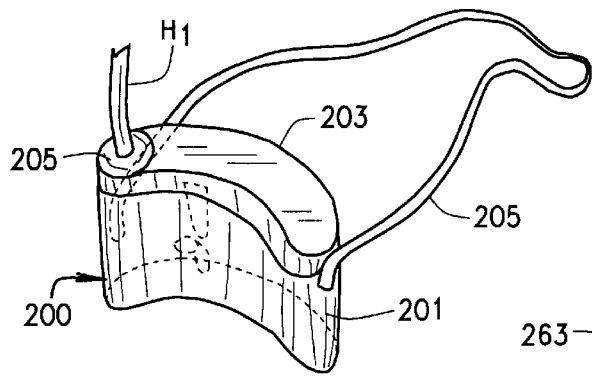
FIG. 12 is a perspective view of a purse-like carrier in which the pressurized container can be placed to be carried by a user.

Turning back to FIG. 1, the container 10 is kidney shaped (i.e., a curved, elongated oval) in top plan, having a top and bottom 20, front and back walls 22, and curved end walls 24. The kidney shape of the container 10 allows for the container 10 to be placed in a carrying case, such as seen in FIG. 12. The carrying case can be made from most any material. For example, it can be made from leather or woven, knitted or wound filament textile yarns. Because the container is molded, the external configuration of the container can be generally any desired shape. For example, the container can be shaped and configured to be received in a fanny pack, or in a holster-type container which could be suspended from a user's belt, as seen in FIGS. 12–18.

A pair of elongate biasing ribs or dividers 28 extend between the front and back walls 22 of the container 10. The ribs 28 define hollow slots 30 in the container 10. The ribs 28 are generally centered with respect to the ends 24 of the container 10, and effectively divide the container into three horizontal sections or passages 12a–c, joined by a pair of vertical passages 12d–e along the end walls of the container.

As noted, the container 10 is molded, and can be molded in any desired configuration, so that it can conform to a desired shape. Further, the ribs or dividers 28 of the container can also be molded in many different configurations. Other possible configurations of the container and ribs are shown in FIGS. 3–5. The container 10A of FIG. 3 includes four ribs or dividers 28A arranged in a 2×2 array. The ribs are kidney shaped in cross-section and define slots 30A extending between the front and back walls of the container 10A. The four ribs 28A define three vertical passages or channels 32V (two outer and one center channel) and three horizontal passages or channels 32H (an upper, a lower, and a center channel) through which the pressurized gas can flow.

The container 10B of FIG. 4 has numerous triangular shaped ribs or dividers 28B which define slots 30B extending between the front and back walls of the container 10B. As seen, the triangular ribs 28B define vertical channels 32V (including two outer channels and a pair of central channels), three horizontal channel 32H (an upper channel, a bottom channel, and a center channel), and several diagonal channels 32D.

Figure 4A:
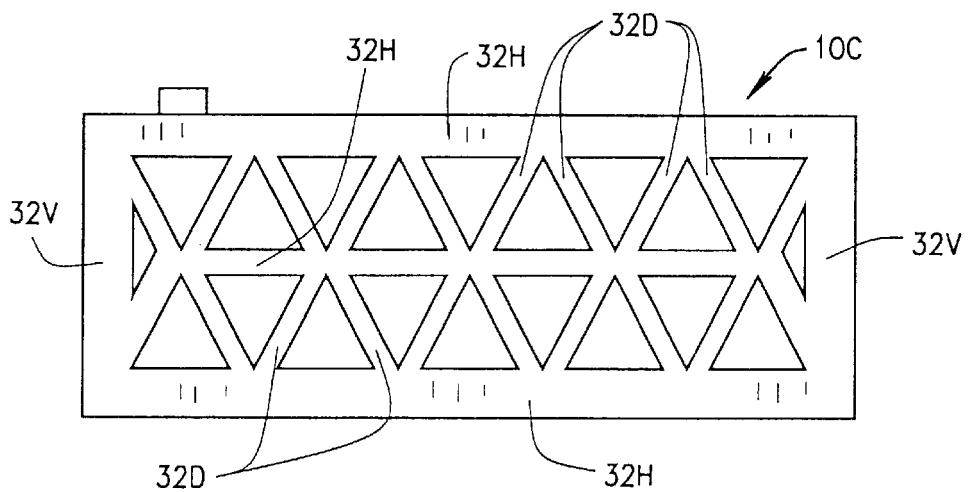
FIG. 4A is a is a side elevational view of further embodiment of the pressurized container.

The container 10C of FIG. 4A is also provided with hollow triangular shaped ribs or dividers 28C, but in a different pattern. The dividers 28C define side vertical channels 32V; upper, lower, and middle horizontal channels 32H; and crisscrossing diagonal channels 32D, all of which are in communication with each other, either directly or indirectly.

The container 10D of FIG. 5 is shown to have nine elongate ribs 28D which define rectangular slots 30D extending between the front and back surfaces of the container. The ribs are arranged in a 3×3 array, and hence define four vertical channels 32V (two outer and two center channels) and four horizontal channels 32H (an upper channel, a bottom channel, and two central channels).

The hollow ribs or dividers in the container provide structural rigidity to the container. Other rib/slot shapes and arrangements can be used. For example, the rib/slots could be circular. Further, although the ribs/slots are shown to have flat or planar side walls, the walls of the ribs/slots could be convex, such that the channels defined by the ribs/slots would be generally circular in cross-section.

The containers 10A–D of FIGS. 1–5 are all static or rigid in shape. That is, they maintain the same shape, regardless of how full or empty they are. To help maintain the shape of the rigid containers, a non-metallic plate can be provided to help maintain the shape of the container. When the container is pressurized, the pressure in the container will tend to cause the container to balloon slightly. After many cycles of use, the container may begin to loose shape. Hence, the walls, for example of the kidney shaped container of FIG. 1 can be reinforced with a non-metallic plate which will, to some degree, counteract the forces of the pressurized gas. Preferably, the material from which the plate is made has a "memory", such that, any deflection in the walls of the container due to pressurization of the container, will be substantially eliminated when the container is empty or depressurized. Thus, this plate will tend to return the container to its original desired shape. It will also help reduce the amount of deflection or ballooning of the container when the container is pressurized. The plate can be made from a material such as Kevlar. Alternatively, it can be made from a rubber or plastic. The plate can be applied to all the surfaces of the container, or only selected surfaces of the container, as may be desired.

The containers shown in FIGS. 6–10, on the other hand, are collapsible. These containers, as discussed below, collapse at least partially when empty, and expend when filled (pressurized). In selecting candidate materials for the collapsible container, it was important to choose a polymeric material that would maintain its elastic property over varying temperature conditions and through many cycles of pressurization and use, without creep or rupture, and at the same time be moldable. Furthermore, it was important that the polymeric material possess high tensile strength, so that it does not deform easily under tensile load due to internal gas pressure. The polymeric materials noted above for the liner 12 all work well with a collapsible/expandable container. Additionally, the collapsible/expandable container is made in substantially the same way as the rigid containers 10–10D. A polymeric liner is initially molded in a desired shape. Preferably, the liner is molded to be in the relaxed or collapsed state. The liner is coated with an adhesive, and a high tensile jacket is wound about the walls of the liner. As with the containers 10–10D, the fiber material is in a thread form, and is wound about the container so that the direction of the thread is perpendicular to the direction of the force exerted by the pressurized gas held within the container.

A first collapsible/expandable container 50 is shown in FIGS. 6 and 7. The container 50 is generally ladder shaped. That is, it has two outer rails 52 and 54 and a plurality of horizontal members or rungs 56 extending between the rails 52 and 54. The rails and rungs are all hollow and communicate with each other, as seen in FIG. 7. The rails 52 and 54 define vertical channels through which gas can flow, and the rungs 56 define horizontal channels through which gas can flow. The channels are all rectangular in cross-section, but could be oval, round, or made to have any other desired cross-sectional shape. The rungs 56 are molded to be generally wavy when in a relaxed state (i.e., when the container is not pressurized). When the container 50 is pressurized (i.e., filled with pressurized gas), the rungs 56 will straighten out, as seen in FIG. 7. For the threads of the reinforcing jacket to reinforce the container of the container 50, the reinforcing threads are wound about the rungs 56 and about the rails 52 and 54, so that the axes of the threads are normal to the axes of the rungs and rails.

Figure 8:
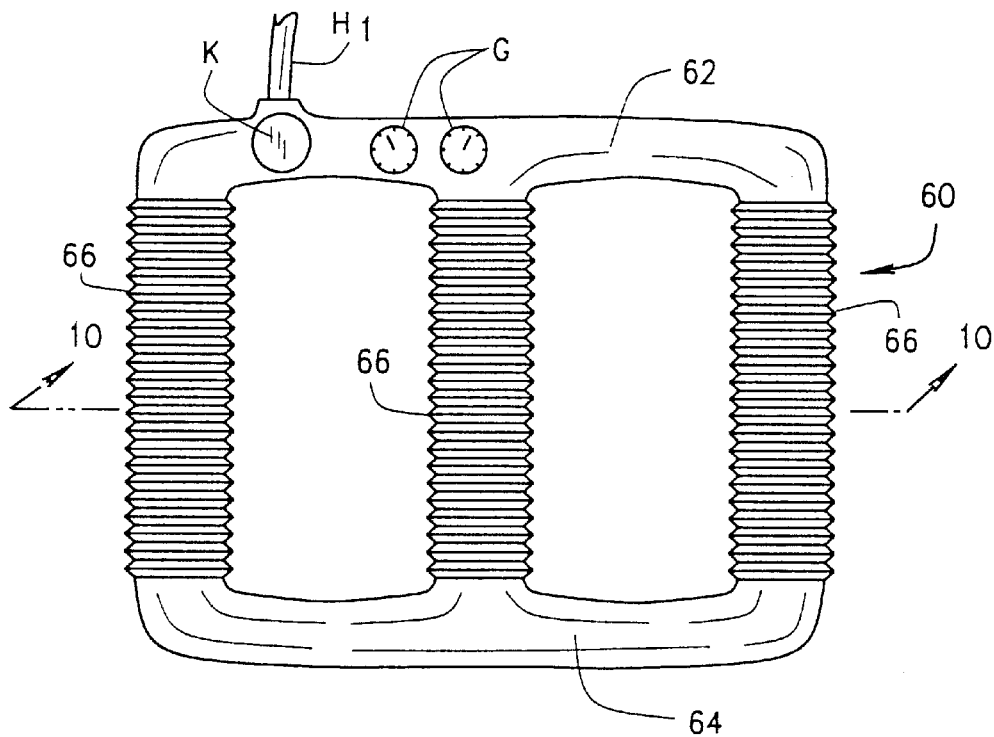
FIG. 8 is an elevational view of alternative embodiment of the expandable/collapsible pressurized container.
Figure 9:
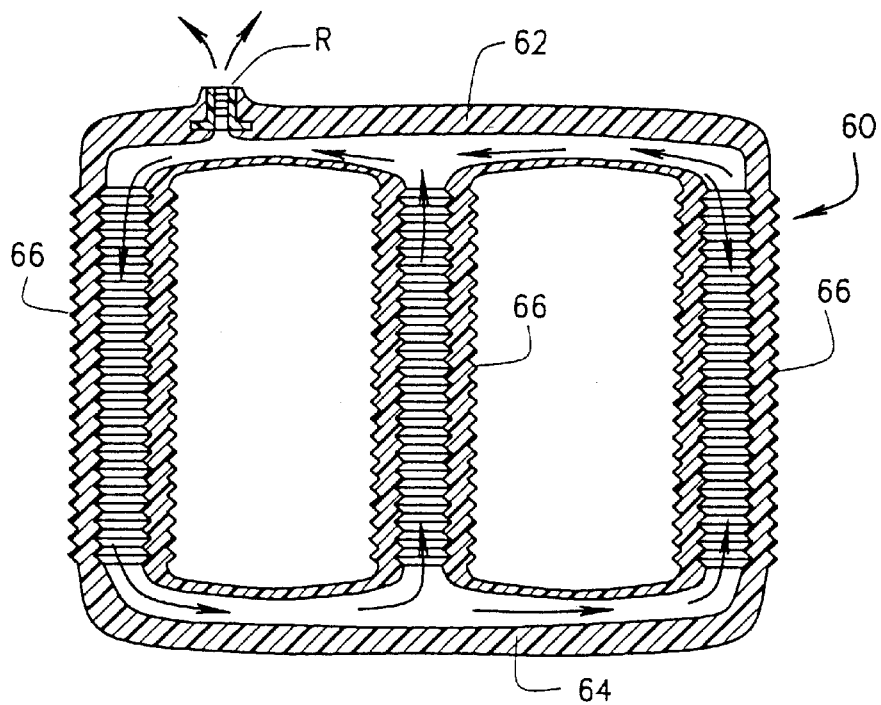
FIG. 9 is a vertical cross-sectional view taken along line 9—9 of FIG. 8.

The container 60 shown in FIGS. 8 and 9 is made in a pillar configuration, as opposed to a ladder configuration. The container 60 includes hollow top and bottom sections 62 and 64 which define horizontal channels, and three hollow posts 66 which extend between the top and bottom sections and define vertical channels which communicate with the horizontal channels. The top and bottom members 62 and 64 are rigid. However, the posts are pleated or accordioned. Hence, the container 60 can be collapsed in a vertical fashion when it is not pressurized. When the container 60 is pressurized, the posts 66 will straighten out, and the container will expand in a vertical direction (with reference to FIGS. 8 and 9). The pleats or accordions of the posts 66 serve a purpose in addition to the expansion and contraction of the posts. The pleats or accordions also act as ribs, which help reinforce the structural integrity of the container 60.

The posts 66 and top and bottom members 62 and 64 are all circular in cross-section, and define interconnecting cylinders. Although they are circular, the posts and top and bottom members could be formed in other shapes. Additionally, more than three posts could be provided, and, in fact, if the top and bottom members were made wide enough, the posts could be arranged in an array.

As seen in FIG. 9, the regulator R of the container 60 is molded into the container, giving the container a low profile regulator, and allowing for the hose H1 to essentially extend from the surface of the container. The regulator R includes a control knob K to allow for adjustment of the flow of gas (oxygen) from the tank. Additionally, the container is provided with gauges G which are in operable communication with the tank. At least one of the gauges is a pressure gauge to show the user the pressure in the container. Other gauges could also be provided. For example, the other gauge shown could be a volume gauge, so that the user would not have to convert pressure into a volume, to enable the user to more easily determine how much gas is left in the container.

Another collapsible/expandable container 70 is shown in FIGS. 10–10B. The container 70 is a columnar container or generally rectangular container having front and back walls 72 and side walls 74 all of which are pleated or accordioned, as seen best in FIGS. 10A and 10B, with pleats or fold lines 76 defining sections of the front and back walls. Although the container 70 is shown to be generally rectangular, it could also be square, round, rectangular, or any other desired shape. The container 70 is made from the same materials, and in the same manner as the containers 10–10D, 50 and 60. Like the containers 50 and 60, because the container 70 is made from flexible materials, and because the reinforcing jacket surrounding the container liner is wound around the front, back, and side walls of the container to be normal to the axis of the container, the container when empty, or unpressurized, will be in a contracted or relaxed state, and will expand when filled with gas and pressurized. Then, during use, as the container is emptied, it will contract to its relaxed state.

The container 70 is shown to have a regulator knob K and gauges G on its top surface. The knob and gauges G of the container 60 were shown on the side surface of the container.

As discussed above, the pressurized containers 50, 60, and 70, move between an expanded state when pressurized, and a contracted or collapsed state when emptied or not pressurized. The containers 50, 60 and 70 are formed in the collapsed state, and hence, the collapsed state of the container is its normal position. Thus, the containers are expanded upon pressurization. The polymer from with the container liner is made has a memory. Thus, as the gas is expelled from the container, the memory of the liner will cause the liner, and hence the container, to collapse towards its normally collapsed position. The threads from which the reinforcing jacket is made are wound about the various sections of the container to reinforce the container against the outwardly directed pressure, exerted by the gas within the container. However, the wrapping of the threads about the container will not interfere with the extension (or expansion) and collapse of the container. The ability of the containers to contract or collapse has several advantages. First, because the containers collapse or contract when empty or unpressurized, they take up less space than when pressurized. Hence, more unpressurized containers can be shipped in a single shipment or stored in a desired location than a traditional container which does not contract. Additionally, because the container contracts as the gas within the container is used, the extent of contraction of the container can serve as a rough indication as to how full the container is. Of course, the extent of contraction cannot be substituted for the meters associated with pressure containers to accurately determine how much gas remains in the container.

The expandable/collapsible containers 50, 60, and 70 and the more rigid containers 10–10D all include various different elements to strengthen them. The containers 10–10D include hollow ribs or dividers which define slots which extend between the front and back walls of the container; the container 50 includes the rungs extending between the side rails; and the containers 60 and 70 include pleats or accordions in their walls. Additionally, the containers 10–10D, 50, and 60 all define multiple channels having at least two side vertical channels which communicate with top and bottom vertical channels. The multiple channels defined by the slot forming ribs 30–30D of containers 10–10D, the rungs 56 of the container 50, and the posts 66 of the container 60 all increase the surface area of the container for a given volume of gas in the container. Although the containers shown all include a top channel, a bottom channel, and two side channels; one of the interconnecting channels could be removed. For example either the top or bottom channel could be removed; or one of the side channels could be removed. For the containers 50 and 60, the channels also provide structural integrity to the container to prevent the rungs 56 or the posts 66 from moving relative to each other significantly. Thus, if one of the connecting channels is removed, it would need to be replaced with a wall to hold the positions of the rungs or posts relative to each other.

As can be appreciated, the containers 10–10D, 50, 60, and 70 are light weight, and hence can be easily carried by a user.

Preferably, the container is sized so that it can fit into a carrying case. The carrying case can take on many forms. It can be a purse-like case (FIGS. 12–15) which is carried over a shoulder, with the strap hanging generally vertically down the user's side, or across the user's body; a back-pack (FIGS. 16–17), or even a waist or fanny-pack (FIG. 18).

Turning to FIG. 12, the carrying case 200 can be seen to be generally kidney shaped, generally matching the shape of the container 10 of FIG. 1. The case 200 has a body 201 and a cover 203, which in combination define a cavity sized and shaped to receive the container. A strap 205 extends from opposite sides of the carrier body 201 to allow the carrier to be carried on a user's shoulder, with the strap 205 either hanging straight down from the shoulder or across the user's body. In other words, the carrier 200 can be carried like a purse. The carrier cover 203 can be opened to gain access to the container within the carrier to allow for adjustment of the regulator knob to control oxygen flow from the container, or to insert or remove the container from the carrier. Additionally, the carrier cover 203 has an opening 205 through which the hose H1 passes. The kidney shape of the carrier 200 conforms the carrier somewhat to the curvature of a user's body, allowing the carrier to be carried comfortably adjacent a user's body.

Figure 13:
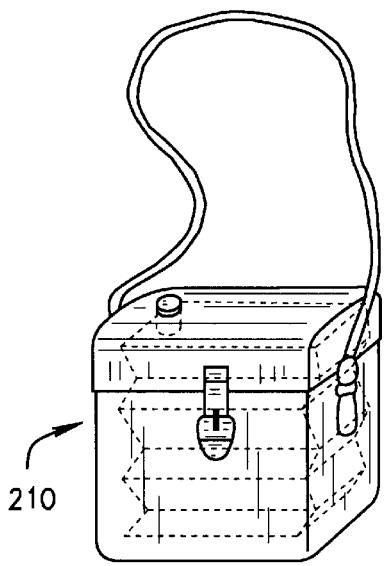
FIG. 13 is a perspective view of another carrying case adapted to hold one of the containers of the present invention; the container being shown in phantom.

As can be appreciated, the shape of the carrying case will vary, depending on the shape of the tank or container. For example, the carrier 210 of FIG. 13 is sized and shaped to receive the container 70. Otherwise, the carrier 210 is generally similar to the carrier 200.

Figure 16:
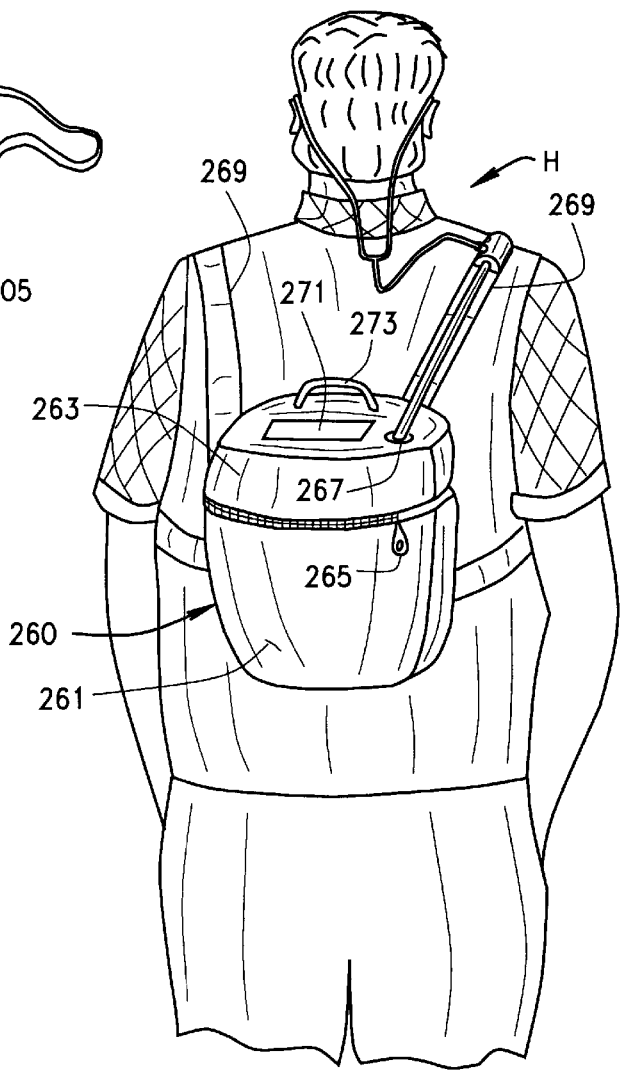
FIG. 16 is a rear elevational view of a person wearing a back-pack carrier for carrying a pressurized container.

An alternative carrying bag 220 is shown in FIG. 14. The carrying bag 220 includes a body 221 and a flap-type cover 223. The cover 223 includes a window 225 to facilitate viewing of the gauges G of the container which indicated the container pressure and for example, the volume of gas remaining in the container. When the cover 223 is opened, the user will have direct access to the regulator control know associated with the container to control the flow of oxygen from the container. A pocket 227 on the side of the container body 221 is sized to hold the hose H1 and the conserver C when the carrier and tank are not in use. An opening (not shown) inside the pocket allows for threading of the hose H1 from the main compartment of the carrier to the pocket 227. A shoulder strap 229 extends up from opposite sides of the top of the body to allow the carrier 220 to be carried. As best seen in FIG. 15A, the strap 229 includes a tube 231 which extends along one side of the strap. The tube 231 includes a slice or groove 233 to allow the hose H1 to be snappingly received in the tube 231. The tube 231 preferably extends a length so that the tube 231 extends from near the base of the strap 229 to a point near the user's shoulder, for example, as seen in FIG. 16. The conserver C could be clipped to the strap 229 on the shoulder. The tube 231 will keep the cannula hose H1 in place, and the hose will not get tangled or pulled. Hence, the user will not need to worry about the hose H1 being pulled from the container.

An alternative carrier 241 is shown in FIG. 15. The carrier 241 is generally similar to the carrier 221, except that its window 243 is on the forward side of the carrier 241. Additionally, instead of having a tube which receives the cannula hose H1, the strap 245 defines a hollow passage 247 through which the hose H1 is threaded, as seen in FIG. 15A. The passage 247 extends generally from base of the strap adjacent the carrier to just about the shoulder of the user. At this point, the passage 247 has an exit and the strap is attached to a shoulder pad 249.

Figure 17:
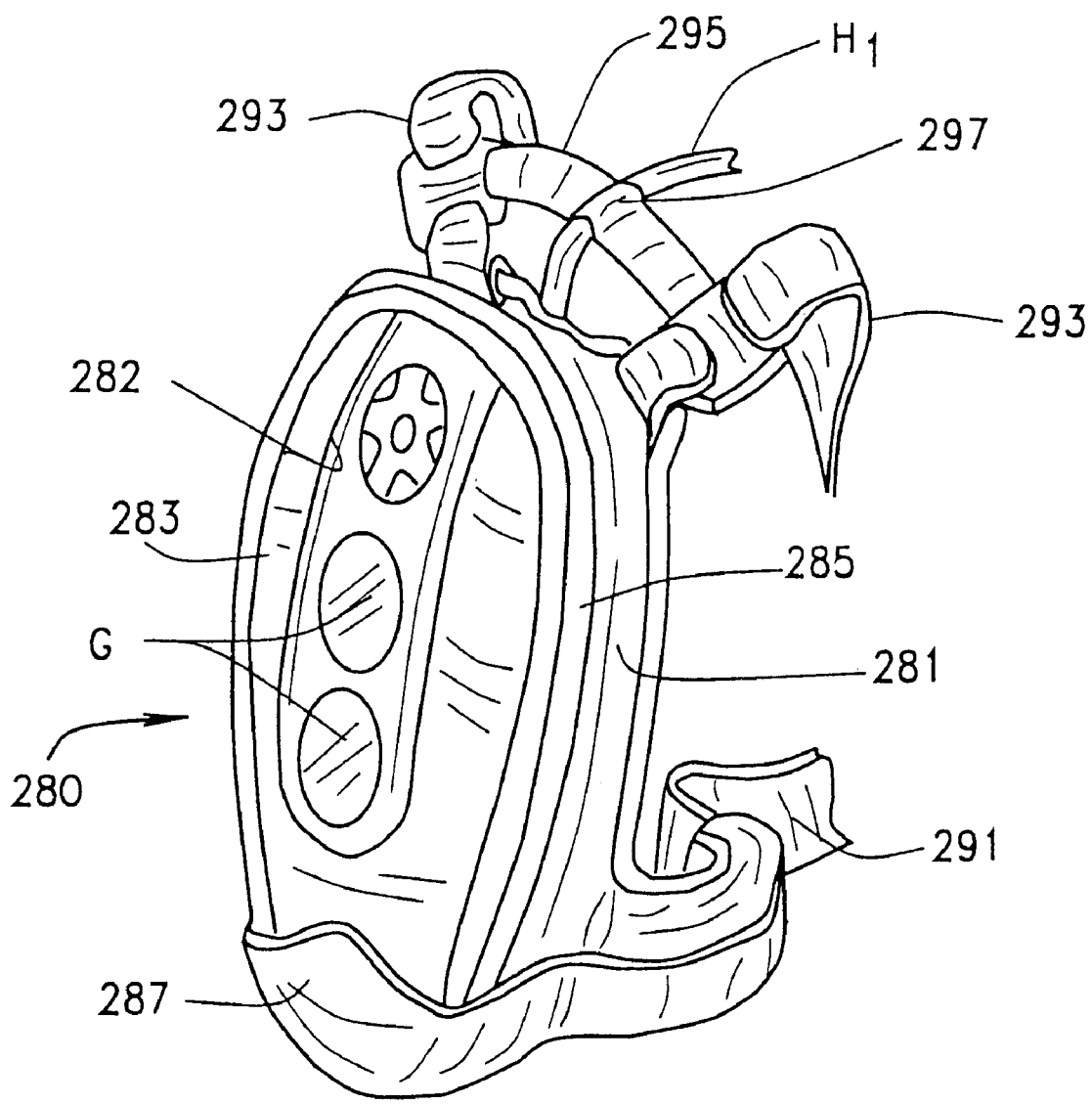
FIG. 17 is a perspective view of an alternative back-pack arrangement for carrying a pressurized container.
Figure 18:
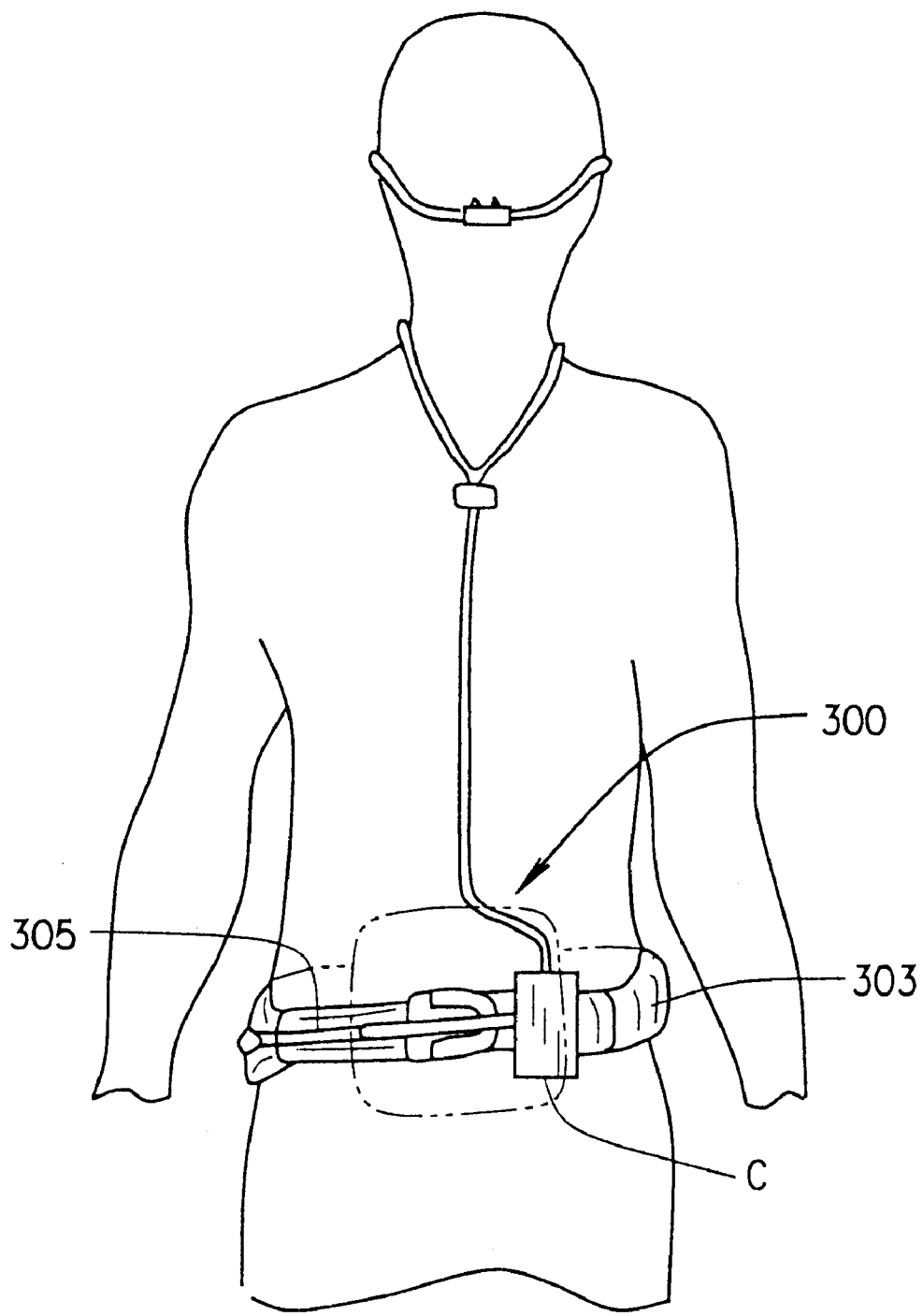
FIG. 18 is a view of a person carrying a container in a waist or fanny pack.

Back pack carriers are shown in FIGS. 16–17. The back pack carrier 260 includes a body 261 and a cover 263 which defines a compartment sized to receive the oxygen container or tank. The cover is shown to be closed by a zipper 265. However, the cover 263 could be closed by any other conventional means, such as a buckle and strap, Velcro strips, snaps, etc. The cover 263 includes an opening 267 through which the hose H1 passes, and, as can be seen, the hose is held to the back pack strap 269 by a tube, identical to the tube 231 of FIG. 14A. The back pack 260 includes a window 271 through which the container gauges can be seen. The back pack also includes a handle 273, or additional strap, on the top of the back pack between the straps 269. The handle 273 allows for hand carrying of the back pack 260.

Another back pack 280 is shown in FIG. 17. The back pack 280 includes a main back portion 281 with a front 283 that opens along a zipper 285. The back pack includes a rigid base 287 to provide more support for the tank or carrier. A window 289 on the front 283 allows for viewing of the gauges G. The back pack is provided with waist straps 291 and shoulder straps 293. A cross-strap 295 extends between the shoulder straps 293. The hose H1 exits the back pack at the top, and near the back, of the back pack. The cross-strap 295 includes a channel or opening 297 through which the hose Hi extends to hold the hose generally in place.

Lastly, a waist or fanny-pack 300 is shown in FIG. 18. The fanny pack 300 includes waist straps 303 which buckle together in the front to hold the pack on the user. One of the straps 303 includes a tube or tunnel 305 through which the cannula hose H1 extends. The conserver can be mounted to the strap 303 spaced slightly from the tunnel exit, or on the other strap; and the hose H2 will extend from the conserver C to the user's nose.

As can be appreciated, although only a few forms of carriers are shown, the carriers can take on many other shapes and sizes. The above are only examples, and show some desired features of the carriers—a window to view the gauges and a tube or tunnel to hold the cannula hose. The various carriers can also be provided with handles, in addition to the straps, to allow for hand carrying of the carriers. Further, the carrier, which is made of a flexible material, such as cloth, vinyl, leather, or the like, can be expandable, for example, by incorporating pleats in the various walls of the carrier. An expandable carrier will be able to expand and contract with the expandable/collapsible containers. Additionally, an expandable carrier can also accommodate different sized, or slightly differently shaped carriers.

As various changes could be made in the above constructions without departing from the scope of the invention, it is intended that all matter contained in the above description or shown in the accompanying drawings shall be interpreted as illustrative and not in a limiting sense. The slots of the individual containers 10–10D are all of the same shape. However, a single container could have slots of different shapes. Thus, a container could include various combinations of rectangular, triangular, and round slots. The rungs 56 of the container 50 are shown to be generally horizontal, but could be altered to be generally vertical. Similarly, the posts 66 of the container 60 are shown to be generally vertical, but could be made to be generally horizontal. As noted above, the container is preferably molded as a unitary, one-piece structure. However, the expandable/contractible containers of containers 50 and 60, could be made of multiple parts. The expandable sections (i.e., the posts 66 of container 60 and the rungs 56 of container 50) could be made independently of the rigid sections (rails 52 and top/bottom channels 62) to which the expandable sections are attached. Although the conserver shown is a pneumatic conserver, the conserver could also be a solid state conserver. The rungs 56 of the container 50 are wavy as shown, and form multiple waves. However, the rungs 56 could define only part of a wave, and hence form a concave or convex arc between the rails 52 and 54. The conserver C of FIG. 11 could be made without the exhalation chamber 105. In this case, the port between the inhalation and exhalation chambers would be omitted, and gas which escapes through the exhalation valve would pass to the atmosphere, rather than to the inhalation chamber. These examples are illustrative only.

What is claimed is:

1. A container for holding gas under pressure,
   said container comprising front, back, side, top, and bottom surfaces defining a chamber for storing gas under pressure; the container comprising at least one rib extending between opposed surfaces of said container and through said chamber; said at least one rib in combination with said container surfaces defining a plurality of channels; said channels all being in fluid communication with each other such that gas in the container can flow freely between the channels; said container surfaces comprising:
   an inner liner molded from a polymer;
   a moisture impervious film surrounding the inner liner;
   reinforcing fibers made from a high-tensile strength material; and an outer coating, said outer coating being made from a material that is non-gas absorbing and which does not readily conduct heat.

2. The container of claim 1 wherein said channels comprise two side channels which are spaced apart from each other.

3. The container of claim 1 wherein said channels comprise a top channel and a bottom channel.

4. The container of claim 1 wherein said at least one rib is generally rectangular, generally kidney shaped, generally triangular, and combinations thereof.

5. The pressurized container of claim 1 wherein said rib is hollow.

6. A container for storing a gas under pressure; the container including flexible walls defining a chamber having a volume; said flexible walls including side walls; said side walls being accordioned; the flexible walls being movable between an expanded state when the container is pressurized and a contracted state when the container is unpressurized, whereby the volume of the chamber decreases as gas is removed from the container; said container being made from a polymeric material wrapped with a high tensile strength fiber material, said fiber being wrapped about said polymeric material such that the axis of the fiber is normal to the direction of expansion and contraction of said container.

7. A container for storing a gas under pressure; the container including
   flexible walls defining a chamber having a volume: the flexible walls being movable between an expanded state when the container is pressurized and a contracted state when the container is unpressurized, whereby the volume of the chamber decreases as gas is removed from the container; said container being made from a polymeric material wrapped with a high tensile strength fiber material, said fiber being wrapped about said polymeric material such that the axis of the fiber is normal to the direction of expansion and contraction of said container;
   interconnected conduits which define at least one generally horizontal channel and at least one generally vertical channel; said horizontal and vertical channels being in fluid communication with each other such that gas in the container can flow freely between the channels; at least one of the horizontal and vertical channels being formed from flexible expandable/contractible conduits which are movable between an expanded state when the container is pressurized and a contracted state when the container is unpressurized; the expandable/contractible conduits being accordioned.

8. A container for storing a gas under pressure; the container including
   flexible walls defining a chamber having a volume; the flexible walls being movable between an expanded state when the container is pressurized and a contracted state when the container is unpressurized, whereby the volume of the chamber decreases as gas is removed from the container; said container being made from a polymeric material wrapped with a high tensile strength fiber material, said fiber being wrapped about said polymeric material such that the axis of the fiber is normal to the direction of expansion and contraction of said container; interconnected conduits which define at least one generally horizontal channel and at least one generally vertical channel; said horizontal and vertical channels being in fluid communication with each other such that gas in the container can flow freely between the channels; at least one of the horizontal and vertical channels being formed from flexible expandable/contractible conduits which are movable between an expanded state when the container is pressurized and a contracted state when the container is unpressurized; wherein the expandable/contractible conduits define at least a portion of a wave when in the contracted state.

9. A container for holding gas under pressure, the container comprising:
   an inner liner molded from a polymer;
   a moisture impervious film surrounding the inner liner;
   reinforcing fibers made from a high-tensile strength material;
   an outer coating, said outer coating being made from a material that is non-gas absorbing and which does not readily conduct heat; and
   a layer of a fire retardant material which surrounds the outer coating.

10. A container for holding gas under pressure, the container comprising:
    an inner liner molded from a polymer;
    a moisture impervious film surrounding the inner liner;
    reinforcing fibers made from a high-tensile strength material; and
    an outer coating, said outer coating being made from a material that is non-gas absorbing and which does not readily conduct heat;
    wherein, when said inner liner is made from carbon fiber, said carbon fiber also comprises said reinforcing fibers.

11. The container of claim 10 wherein the polymer for the inner liner is chosen from a linear low-density polyethylene (LLDPE), a low-density polyethylene (LDPE), nylon, a polyolefin-based polymer having a carbon filler, or a carbon fiber or resin/fiber matrix.

12. The container of claim 10 wherein the liner has a thickness of between about 0.05" and about 0.07".

13. The container of claim 10 wherein the reinforcing fibers are formed as a jacket surrounding the inner liner.

14. The container of claim 10 wherein said outer coating is made from fluorocarbon, polyurethane, or other moisture impervious and insulating materials.

* * * * *